(12) United States Patent
Kufer et al.

(10) Patent No.: US 7,491,814 B2
(45) Date of Patent: Feb. 17, 2009

(54) REAL-TIME RT-PCR FOR THE SENSITIVE DETECTION OF MULTIPLE MAGE GENE TRANSCRIPTS

(76) Inventors: Peter Kufer, Am Kapellenacker 13, D-85368 Moosburg (DE); Ingo Mecklenburg, Maron-Str. 10, D-81373 München (DE)

( * ) Notice: Subject to any disclaimer, the term of this patent is extended or adjusted under 35 U.S.C. 154(b) by 0 days.

(21) Appl. No.: 10/536,932

(22) PCT Filed: Nov. 28, 2003

(86) PCT No.: PCT/EP03/13415
§ 371 (c)(1),
(2), (4) Date: Nov. 22, 2005

(87) PCT Pub. No.: WO2004/048608
PCT Pub. Date: Jun. 10, 2004

(65) Prior Publication Data
US 2006/0147928 A1   Jul. 6, 2006

(30) Foreign Application Priority Data
Nov. 28, 2002   (EP) ................................ 02026584

(51) Int. Cl.
*C07H 21/04* (2006.01)
*C12P 19/34* (2006.01)
(52) U.S. Cl. .................................. 536/24.33; 435/91.2
(58) Field of Classification Search .................. None
See application file for complete search history.

(56) References Cited

U.S. PATENT DOCUMENTS

| | | | | |
|---|---|---|---|---|
| 5,386,022 | A * | 1/1995 | Sninsky et al. | 536/24.32 |
| 6,057,105 | A * | 5/2000 | Hoon et al. | 435/6 |
| 6,221,593 | B1 * | 4/2001 | Boon-Falleur et al. | 435/6 |
| 6,537,777 | B1 * | 3/2003 | Gellerfors et al. | 435/69.1 |
| 6,686,147 | B1 * | 2/2004 | Scanlan et al. | 435/6 |
| 6,691,041 | B2 * | 2/2004 | Sagner et al. | 702/19 |
| 2006/0051324 | A1 * | 3/2006 | Kirkin et al. | 424/93.7 |

FOREIGN PATENT DOCUMENTS

WO    WO 98/46788    10/1998

OTHER PUBLICATIONS

Buck et al., "Design Strategies and Performance of Custom DNA Sequencing Primers," Biotechniques, Sep. 1999, vol. 27, No. 3, pp. 528-536.*
De Plaen et al., "Structure, chromosomal localization, and expression of 12 genes of the MAGE family," *Immunogenetics*, 40:360-369, 1994.
Kufer et al., "Heterogeneous expression of MAGE-A genes in occult disseminated tumor cells: a novel multimarker reverse transcription-polymerase chain reaction for diagnosis of micrometastatic disease," *Cancer Res.*, 62:251-261, 2002.
Otte et al., "MAGE-A gene expression pattern in primary breast cancer," *Cancer Res.*, 61:6682-6687, 2001.
Park et al., "A new strategy for the diagnosis of MAGE-expressing cancers," *J. Immunol. Methods*, 266:79-86, 2002.
Riker et al., "Threshold levels of gene expression of the melanoma antigen gp100 correlate with tumor cell recognition by cytotoxic T lymphocytes," *Int. J. Cancer.*, 86:818-826, 2000.
Sasaki et al., "MAGE-E1, a new member of the melanoma-associated antigen gene family and its expression in human glioma," *Cancer Res.*, 61:4809-4814, 2001.
Scanlon et al., "Identification of cancer/testis genes by database mining and mRNA expression analysis," *Int. J. Cancer*, 98:485-492, 2002.
Yoshioka et al., "Real-time rapid reverse transcriptase-polymerase chain reaction for intraoperative diagnosis of lymph node micrometastasis: clinical application for cervical lymph node dissection in esophageal cancers," *Surgery*, 132:34-40, 2002.

* cited by examiner

*Primary Examiner*—Kenneth R. Horlick
*Assistant Examiner*—Molly E Baughman
(74) *Attorney, Agent, or Firm*—Fulbright & Jaworski, LLP

(57) ABSTRACT

The present invention relates to a highly sensitive real-time RT-PCR method for specifically detecting the expression of more than one MAGE gene. The present invention further relates to a diagnostic composition for carrying out such a real-time RT-PCR as well as to oligonucleotides suitable for the cDNA synthesis reaction prior to real-time PCR amplification of more than one marker from the MAGE gene family. To enable the quantitative measurement of MAGE gene expression in a clinical sample an RT-protocol was invented using very sophisticated non-standard conditions to accomplish real-time PCR amplification of cDNA of several MAGE family members in relation to a comparative normalizing reference gene as internal control.

9 Claims, 6 Drawing Sheets

Figure 2:
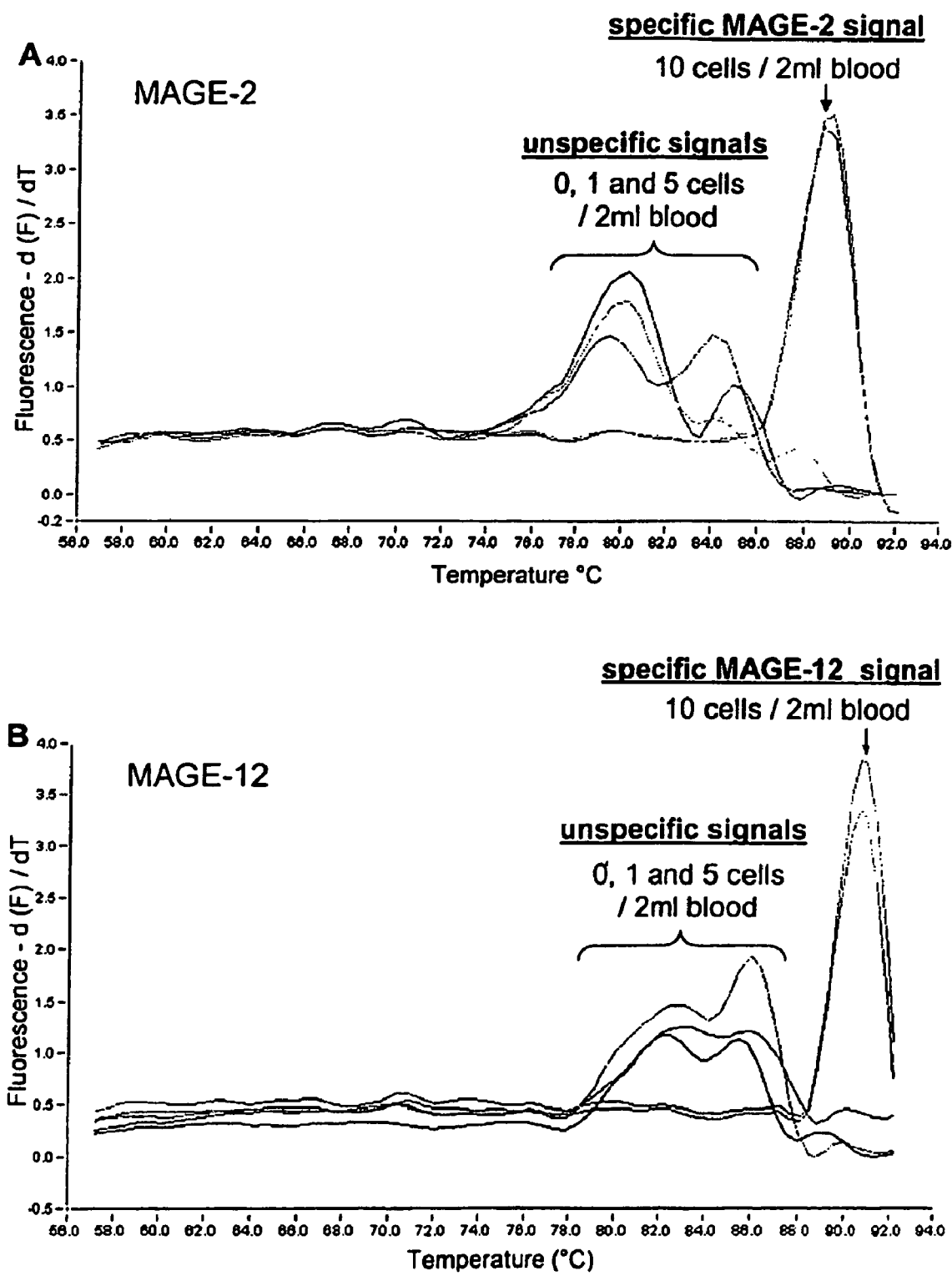

Figure 1
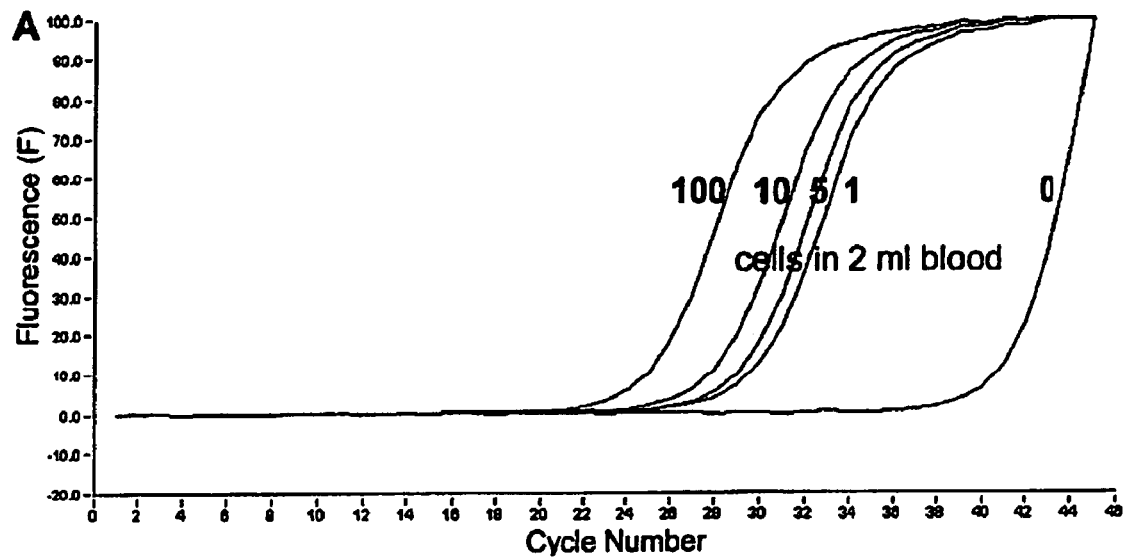
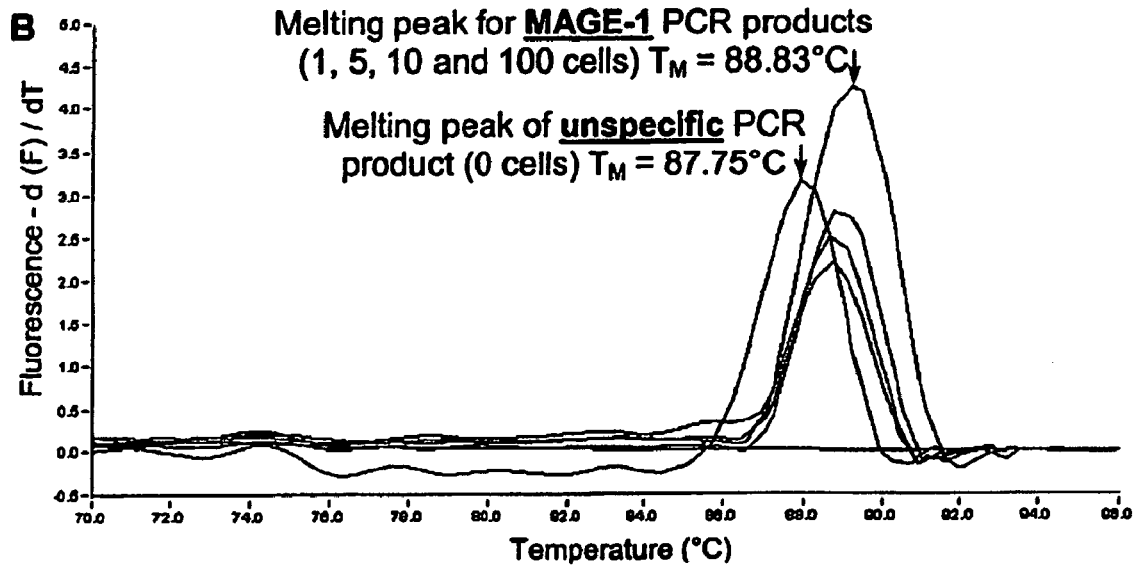
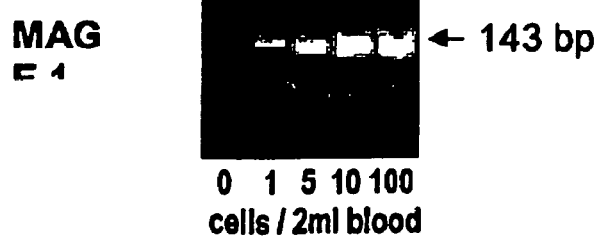

SEQUENCE LISTING

```
<160> NUMBER OF SEQ ID NOS: 93

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ccagcatttc tgcctttgtg a                                                  21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
ccagcatttc tgcctgtttg                                                    20

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
cagctcctcc cagattt                                                       17

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
acctgccggt actccagg                                                      18
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
acctgccggt actccaggta                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gcccttggac cccacaggaa                                                    20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
aggactttca catagctggt ttca                                               24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggactttcac atagctggtt tc                                                 22

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
tttattcaga tttaatttc                                                     19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
caagagacat gatgactctc                                                    20
```

-continued

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ttcctcaggc ttgcagtgca                                                 20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gagaggagga ggaggtggc                                                  19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
gatctgttga cccagcagtg                                                 20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
cactgggttg cctctgtc                                                   18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
ctgggttgcc tctgtcgag                                                  19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
gggttgcctc tgtcgagtg                                                  19

<210> SEQ ID NO 17
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ggctgctgga accctcac                                                   18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gcttggcccc tcctcttcac                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gaacaaggac tccaggatac                                                 20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
catacatgca ttcctcaggg t                                               21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gaactttctc tgcagctggg c                                               21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
tggcagggtt tctagggtct                                                 20

<210> SEQ ID NO 23
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
ggtttccccg aatactcctg                                                  20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
ttgctaggat gatggcactg                                                  20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ccaagatgtc ctggtccttg                                                  20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
cagcacaccc accagatc                                                    18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
agagtctcgg gatcgtgc                                                    18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
agtctcggga tcgtgcag                                                    18

<210> SEQ ID NO 29
<211> LENGTH: 18
<212> TYPE: DNA
```

<213> ORGANISM: Artificial Sequence
<220> FEATURE:
<223> OTHER INFORMATION: Description of Artificial Sequence: Synthetic
      Primer

<400> SEQUENCE: 29
tctcgggatc gtgcagca                                                      18

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
atgcagcgaa gcagagtct                                                     19

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
cctttcagcg atgcagcg                                                      18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
gtatgcacgg ctactggc                                                      18

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
gctatctgag ccgtctagac                                                    20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
aatgttacga gcagtgatgc                                                    20

<210> SEQ ID NO 35
<211> LENGTH: 18
<212> TYPE: DNA
<213> ORGANISM: Artificial Sequence

```
<220> FEATURE:
<223> OTHER INFORMATION: Description of Artificial Sequence: Synthetic
      Primer

<400> SEQUENCE: 35
tggggccctg ctggaatg                                                  18

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
cagttaatgg gcatcgttaa g                                              21

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
atctgtgccc cacaaaccag                                                20

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
ggcccgggat gtaggcac                                                  18

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
ggtaatcact ccccagatag                                                20

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
ctcccggggt aatcactc                                                  18

<210> SEQ ID NO 41
<211> LENGTH: 18
<212> TYPE: DNA
<213> ORGANISM: Artificial Sequence
<220> FEATURE:
```

<223> OTHER INFORMATION: Description of Artificial Sequence: Synthetic
      Primer

<400> SEQUENCE: 41
cagtctcccg gggtaatc                                                    18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
tgaggaggca aggcagtc                                                    18

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
ggattggtta cattcaaagg c                                                21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
agagtgattc gcgtgggtac c                                                21

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
ggctgcaacg gcggaagaaa ac                                               22

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
tgcaacggcg gaagaaaac                                                   19

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic

```
                            Primer

<400> SEQUENCE: 47
atgtctggta acggcaatgc                                              20

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
ttgcagatgg ctccgatggt gaa                                          23

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
ggctccgatg gtgaagcc                                                18

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
ttgggtgaaa gacaacagca tc                                           22

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
gtagagttcg gccgaaggaa c                                            21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52
caggagctgg gcaatgaaga c                                            21

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 53
cattgaagga gaagatctgc ct                                              22

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54
gagtagaaga agaagcggt                                                  19

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 55
gaagccggcc caggctcg                                                   18

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
gatgactctg gtcagggcaa                                                 20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
caccaaggag aagatctgcc t                                               21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58
tcctcagtag taggagcctg t                                               21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 59
ctacagacac agtgggtcgc                                              20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60
gcttggtatt agaggatagc ag                                           22

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 61
tccgtgagga ggcaaggttc                                              20

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 62
atcggattga ctccagagag ta                                           22

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 63
tagagttcgg ccgaaggaac                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 64
ctgggcaatg aagacccaca                                              20

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 65
```
cattgaagga gaagatctgc ct                                                    22

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 66
caggcttgca gtgctgactc                                                       20

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 67
ggctcggtga ggaggcaag                                                        19

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 68
gatgactctg gtcagggcaa                                                       20

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 69
caccaaggag aagatctgcc t                                                     21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 70
caggcttgca gtgctgactc t                                                     21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 71

```
atctgacaag agtccaggtt c                                              21

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 72
cgctgacgct ttggagctc                                                 19

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 73
tccgtgagga ggcaaggttc                                                20

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 74
gagcctgcgc acccaccaa                                                 19

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 75
ttgcagatgg ctccgatggt gaag                                           24

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 76
aactcctgct gctcgtccag                                                20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 77
ttgtgccagc ccatgcgctg                                                20
```

```
<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 78
agcttccgaa gccgggtg                                                   18

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 79
cttggctgcc acttccacg                                                  19

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 80
gcagggacat ggatggtag                                                  19

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 81
agccaactgg ggccctcg                                                   18

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 82
taagctgccg tgcaacatcc                                                 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 83
ctacagacac agtgggtcgc                                                 20
```

```
<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 84
gcaggatctg acaagagtcc                                                   20

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 85
atctgacaag agtccaggtc c                                                 21

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 86
tgggagtgtg ggcaggact                                                    19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 87
cgctgacgct ttggagctc                                                    19

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 88
atcctcctcc acagccagg                                                    19

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 89
ggagctggtg gaagtggatg                                                   20
```

```
<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 90
gcttggtatt agaggatagc ag                                              22

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 91
catcagcaga aacctcctct g                                               21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 92
aatggaaggg aagcaacgac c                                               21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 93
ggagccctca tcagattgat c                                               21
```

REAL-TIME RT-PCR FOR THE SENSITIVE DETECTION OF MULTIPLE MAGE GENE TRANSCRIPTS

This application is a national phase application under 35 U.S.C. § 371 of International Application No. PCT/EP 2003/013415 filed 28 Nov. 2003. The entire text of each of the above-referenced disclosures is specifically incorporated herein by reference without disclaimer.

The present invention relates to a highly sensitive real-time RT-PCR method for specifically detecting the expression of more than one MAGE gene. The present invention further relates to a diagnostic composition for carrying out such a real-time RT-PCR as well as to oligonucleotides suitable for the cDNA synthesis reaction prior to real-time PCR amplification of more than one marker from the MAGE gene family.

The MAGE gene family was originally described in melanoma patients when cytolytic lymphocytes specific for the MAGE-A1 gene product were identified (van der Bruggen, Traversari et al. 1991). This gene was later found to belong to a cluster of 12 human MAGE-A genes located in the q28 region of the X chromosome and more recently other members of the family characterized as subfamilies MAGE-B, -C and -D were described (Chomez, De Backer et al. 2001). The biological function of MAGE gene products is not yet completely understood, but it is assumed that the genes play an important role in tissue regeneration and differentiation (Old 2001).

Selected members of the MAGE gene family (Table 1) are frequently expressed in many tumors almost irrespective of the histological origin but are completely silent in normal adult tissue with the single exception of testicular germ cells (De Plaen, Arden et al. 1994). Several MAGE gene products have been identified as promising targets for tumor immunotherapy and have already been used in vaccination trials. The gene products of MAGE-A1, -A2, -A3, -A4, -A6, -A10 and -A12 are frequently found to induce a cytolytic T-cell response in tumor patients and are therefore the most promising candidates to serve as specific indicators for cancer.

Recently, the exceptionally restricted expression of MAGE-A genes was exploited to develop a highly sensitive and tumor-specific multimarker nested RT-PCR based on the independent conventional amplification of MAGE-A1, -2, -3/6, -4 and -12, respectively (WO 98/46788). This approach was successfully applied for the sensitive detection of rare disseminated tumor cells in blood and bone marrow of various tumor patients with many different types of cancer (Kufer 2002). Others have established sensitive conventional MAGE-PCR methods by use of consensus oligonucleotides that coamplify cDNA of several different MAGE genes (Park, Kwon et al. 2002). Such a pan-MAGE-PCR may also detect rare disseminated tumor cells with high sensitivity. However, it does not provide information on the MAGE gene expression pattern in individual cancer patients, as obtained with a multimarker MAGE PCR specifically amplifying several different individual members of the MAGE family.

Over the past decade the PCR technology made substantial progress through the development of rapid thermocylers and the introduction of fluorescence monitoring of amplified products after each cycle, enabling the quantification of gene expression with "rapid-cycle real-time PCR" assays (e.g. LightCycler® System, ABI PRISM® Sequence Detection System). Sensitive quantification of gene expression thereby relies on the detection of increasing fluorescence during the exponential phase of PCR proportional to the amount of nucleic acids in the sample at the beginning of the reaction. Quantification is based on the threshold cycle ($C_T$-value), the first cycle with detectable fluorescence, and can be performed in absolute manner with external standards or in relative manner with a comparative normalizing reference gene serving as internal calibrator. The determination of a non-inducable reference gene is a critical issue in real-time PCR, since even marginal variations in gene expression will inevitably alter the relative quantification profile of the target gene. Usually genes like glyceraldehyd-3-phospat dehydrogenase (GAPDH), porphobilinogen desaminase (PBGD), beta2-microglobin or beta-actin are frequently used as internal calibrators in real-time PCR. In comparison to conventional end-point PCR the real-time assays display even higher sensitivity and precision as well as a shorter turnaround time for rapid analysis of the results. In general the fluorescence can be detected sequence-specific by use of hybridization probes or TaqMan® probes or sequence-unspecific by use of the SYBR Green I dye.

Recently, single MAGE markers have been amplified by use of the real-time PCR technique: Scanlan and coworkers (Scanlan, Gordon et al. 2002) investigated MAGE-A3 gene expression in tumor tissue by designing a gene-specific TaqMan probe for measuring mRNA quantity using an ABI 7700 sequence detection system. The group of Yoshioka (Yoshioka, Fujiwara et al. 2002) developed a real-time PCR including again the amplification of MAGE-A3 mRNA to screen for tumor cells in resected lymph nodes of cancer patients. Until today, however, there is no real-time PCR for utilizing the gene expression of multiple MAGE markers for quantification of minimal residual tumor disease in cancer patients who have undergone successful treatment of their primary tumor but are at risk of developing distant metastasis growing from the seed of early disseminated tumor cells; these patients, whose tumor load can be advantageously determined by the method of the present invention, urgently need an adjuvant tumor therapy to prevent the seed of metastasis from growing.

The investigation of only single markers is bound to result in a dramatic loss of sensitivity, because of the expression heterogeneity of malignant tumors in general and of single disseminated tumor cells in particular. For these reasons a multimarker real-time RT-PCR method for the highly sensitive detection of multiple tumor relevant markers selected from the MAGE family, like e.g. MAGE-A1, -A2, -A3, -A4, -A6, -A10 and -A12, was highly preferable.

Accordingly, the present invention relates to a highly sensitive real-time RT-PCR for the specific and reliable detection of mRNA transcribed by rare tumor cells from more than one MAGE gene. On the one hand, PCR-primers described in the prior art (Kufer 2002; Park, Kwon et al. 2002) for conventional highly sensitive pan- or multimarker-MAGE amplification methods are also applicable for highly sensitive real-time RT-PCRs. On the other hand, however, methods for reverse transcription of mRNA as successfully used for conventional highly sensitive pan- or multimarker-MAGE RT-PCRs—unexpected from the prior art—turned out to be insufficient for corresponding highly sensitive real-time RT-PCRs.

Since those RT-PCRs designed to detect rare tumor cells, which rely on the amplification of a single marker gene only, are particularly susceptible to expression loss or down-regulation connected with the genomic instability and phenotypic heterogeneity of tumor cells, reliable detection of at least two different MAGE gene transcripts by the real-time RT-PCR of the present invention was absolutely required. Therefore, it is essential to make sure that each single member of the MAGE family selected as a marker for the highly sensitive real-time RT-PCR is reliably converted from mRNA to cDNA by reverse transcription with reproducible efficiency. Only under this prerequisite the relative content in biological samples to be analyzed of the different MAGE mRNA species compared to each other can be determined or quantification of the different MAGE transcripts carried out in comparison to an internal calibrator template like the PBGD mRNA.

As a solution to this technical problem it has been found in the present invention, that reverse transcription of the different MAGE transcripts and optionally of the calibrator mRNA must be carried out simultaneously in a single cDNA-synthesis reaction, using highly selected oligonucleotide primers and sophisticated reaction conditions for reverse transcription, which could not be anticipated from the prior art.

Accordingly the present invention relates to a highly sensitive real-time RT-PCR capable of specifically detecting the expression of more than one MAGE gene, wherein reverse transcription of the corresponding MAGE transcripts is carried out simultaneously in a single cDNA-synthesis reaction. Carrying out efficient and reliable reverse transcription of different transcripts in a single cDNA-sythesis reaction was no trivial task, because the methods for reverse transcription (RT) of two or more different MAGE transcripts, which according to the prior art led to the reliable conversion of each single species of MAGE-mRNA into sufficient cDNA detectable by highly sensitive conventional PCRs, suprisingly failed to do so in combination with a highly sensitive real-time MAGE-PCR. Neither unspecific reverse transcription using cDNA-priming with oligo-dT or random hexanucleotides nor specific cDNA-priming with an established combination of mono- and dual-specific oligonucleotides hybridizing to the different MAGE-transcripts, respectively, proved to be sufficient for obtaining specific amplification products at the desired high sensitivity level for each member of the MAGE family selected as marker for the subsequent real-time PCR (Example 2). Even the use of a "pan-MAGE-primer" for cDNA-synthesis as taught by the closest prior art. (WO 98/46788) disclosing a highly sensitive conventional multimarker MAGE RT-PCR did not succeed under standard conditions in sufficient reverse transcription of mRNA from every single MAGE gene used as marker in the corresponding real-time multimarker MAGE RT-PCR. Thus, it is required, in accordance with the present invention, to identify by careful testing under many different reaction conditions one or more primers for reverse transcription (=RT-primer), each hybridizing to the mRNA of one or more different members of the MAGE gene family. It is essential that the testing of RT-primers for the highly sensitive real-time MAGE RT-PCR is carried out in the presence of the whole cocktail of RT-primers during cDNA-synthesis. This is required because of frequent interferences among different RT-primers, which are neither predictable from cDNA-synthesis reactions with only one RT-primer nor from the teachings of the prior art.

A real-time MAGE PCR, i.e. PCR-amplification of reverse transcribed MAGE-cDNA, in accordance with the present invention, can be implemented either by using a sequence unspecific DNA-dye like SYBR Green I or by applying sequence-defined fluorescent probes for the detection of specific amplicons. For carrying out the latter method, the sequences of MAGE mRNA molecules have to be screened for unique marker-defining regions if the detection of individual MAGE parameters is desired or pan-MAGE specific areas if the detection of several MAGE markers is desired in a single reaction. This unique hybridization region on the sequence must be located in between two oligonucleotides used as primers for the PCR and should neither be self-complementary, monotonous, or repetitive nor complementary to the PCR primers. The application of TaqMan probes requires the design of a single double-labeled fluorescent probe, for the application of hybridization probes the design of two fluorescent oligonucleotides is needed that hybridize in close proximity (1 to 5 bases) to each other on the amplicon to enable the distance-dependent transfer of energy between the fluorophores (fluorescence resonance energy transfer). The reaction conditions have to be carefully evaluated and optimized, involving the adaptation of primer and probe concentrations, temperatures and duration of PCR-cycling etc.

In a preferred embodiment of the method of the invention the MAGE genes serving as markers in a highly sensitive real-time RT-PCR are selected from the functional genes of MAGE subfamilies A, B and/or C (Table 1). Except for the pseudogenes, expression of the members of these MAGE-subfamilies is highly restricted to tumor cells, while they are completely silent in normal adult tissue with the only exception of testicular germ cells. Thus expression of functional MAGE A, B and/or C genes as detected by the highly sensitive real-time RT-PCR of the invention in blood, bone marrow, lymph nodes or other secondary organs of a tumor patient is highly indicative of the systemic spread of cancer cells from the primary tumor. Because of its quantitative nature, the highly sensitive real-time RT-PCR of the invention is particularly useful for measuring the load of disseminated tumor cells in individual patients, thus estimating the risk of a metastatic relapse originating from the early tumor cell spread that took place prior to successful treatment of the primary tumor. Thus, the method of the invention may help to decide more precisely on the requirement of an adjuvant tumor therapy than is possible with diagnostic methods of the prior art.

Besides blood and bone marrow many kinds of body fluids or tissues, like urine, stool or sputum, are easily accessible to search for malignant cells. The real-time MAGE RT-PCR of the present invention is therefore also applicable as highly sensitive screening tool in secondary tumor prevention and can achieve the early detection of neoplasia particularly in individuals who are highly at risk of developing cancer.

In a particularly preferred embodiment of the method of the present invention the MAGE genes serving as markers in a highly sensitive real-time RT-PCR comprise MAGE-A 1, 2, 3, 4, 6, 10 and/or 12. These genes are most frequently expressed in many different types of tumors of various histological origins. Moreover, all members of this selected group of MAGE genes encode target antigens for cytotoxic T cells. Thus, the highly sensitive real-time RT-PCR of the invention will advantageously provide quantitative MAGE gene expression profiles of individual cancer patients as a basis for the rational design of MAGE-based tumor vaccines. So far, only qualitative patterns of MAGE gene expression could be obtained by using prior art methods making the choice of MAGE gene products to be included in a tumor vaccine more difficult.

In another preferred embodiment of the method of the invention at least one primer for reverse transcription of MAGE mRNA is selected from the following groups of oligonucleotides:

| Primer | Sequence (5' - 3') | SEQ ID NO |
|---|---|---|
| (A) | | |
| MgRT1a | CCA GCA TTT CTG CCT TTG TGA | 1 |
| MgRT1B | CCA GCA TTT CTG CCT GTT TG | 2 |
| MgRT2 | CAG CTC CTC CCA GAT TT | 3 |
| MgRT3a | ACC TGC CGG TAC TCC AGG | 4 |
| MgRT3b | ACC TGC CGG TAC TCC AGG TA | 5 |

-continued

| Primer | Sequence (5' - 3') | SEQ ID NO |
|---|---|---|
| MgRT4 | GCC CTT GGA CCC CAC AGG AA | 6 |
| MgRT5a | AGG ACT TTC ACA TAG CTG GTT TCA | 7 |
| MgRT5b | GGA CTT TCA CAT AGC TGG TTT C | 8 |
| MgRT6 | TTT ATT CAG ATT TAA TTT C | 9 |
| (B) | | |
| Mg1_RT1 | CAA GAG ACA TGA TGA CTC TC | 10 |
| Mg1_RT2 | TTC CTC AGG CTT GCA GTG CA | 11 |
| Mg1_RT3 | GAG AGG AGG AGG AGG TGG C | 12 |
| Mg1_RT4 | GAT CTG TTG ACC CAG CAG TG | 13 |
| Mg1_RT5a | CAC TGG GTT GCC TCT GTC | 14 |
| Mg1_RT5c | CTG GGT TGC CTC TGT CGA G | 15 |
| Mg1_RT5d | GGG TTG CCT CTG TCG AGT G | 16 |
| Mg1_RT5e | GGC TGC TGG AAC CCT CAC | 17 |
| Mg1_RT6 | GCT TGG CCC CTC CTC TTC AC | 18 |
| Mg1_RT7 | GAA CAA GGA CTC CAG GAT AC | 19 |

Primers for reverse transcription as depicted in group A, are perfectly matching with each of the mRNA-sequences of MAGE-A 1, 2, 3, 4, 6, 10 and 12. However, most surprisingly, despite the perfect match, none of these RT-primers alone leads to sensitive detection of MAGE-A 1 expression by real-time RT-PCR under standard conditions as provided e.g. by the manufacturer of the LightCycler System. Under these recommended conditions the weakness in detection of MAGE-A 1 expression can only be compensated, as surprisingly found in the present invention, by combining two primers of group A with each other (e.g. MgRT3a+MgRT5a) or a group A-primer with one of the group B-primers, which are monospecific for the cDNA-synthesis of MAGE-A 1 only (Example 2). Depending on which at least two different members of the MAGE-A group encoding target antigens for cytotoxic T cells (i.e. MAGE-A 1, 2, 3, 4, 6, 10 and 12) are to be detected by real-time RT-PCR, different single RT-primers or combinations of RT-primers of group A and/or B may be applicable. In any individual case, however, in accordance with the present invention, careful testing of candidate RT-primers is required to end up with an optimal choice allowing the expression of the selected MAGE genes to be detected by real-time RT-PCR with a high level of sensitivity. As pointed out above, testing of RT-primers for the highly sensitive real-time MAGE RT-PCR has to be carried out in the presence of the whole cocktail of RT-primers during cDNA-synthesis, in order to cope with the unpredictable interferences among different RT-primers.

According to the teaching of the prior art (WO 98/46788) the average expert may—without undue burden—identify specific primers for the cDNA-synthesis that efficiently hybridize to the mRNA of MAGE-1, -2, -3/6, -4 and -12. However, the whole series of "pan-MAGE primers" as depicted in group A failed to result in cDNA-synthesis, which would have allowed the highly sensitive detection of each single marker mRNA by real-time PCR as carried out according to the recommended protocol provided by the manufacturer of the LightCycler System (Roche). In every tested case the highly sensitive detection by real-time PCR of at least one mRNA-species from the group consisting of MAGE-1, -2, -3/6, -4 and -12 failed despite perfect hybridization of every pan-MAGE cDNA-primer to each of the corresponding transcripts (example 2). This clearly differs from the teaching of the above mentioned prior art document referring to a conventional multimarker MAGE RT-PCR.

In a further particularly preferred embodiment of the method of the present invention, in addition to the reverse transcription of MAGE transcripts, reverse transcription of a calibrator mRNA is simultaneously carried out in the same single cDNA-synthesis reaction followed by PCR-amplification of MAGE- and calibrator cDNAs. For making the quantitative results obtained by analysis of different blood-, bone marrow- or other tissue samples from one or more cancer patients using the real-time MAGE RT-PCR comparable with each other, a normalizing reference gene, in accordance with the present invention, is preferably included in the assay. In order to be capable of serving as internal calibrator the normalizing reference marker most preferably is an essentially non-inducible gene. It is further preferred that the expression level of the reference gene is comparable to the target gene(s) and constant in essentially all cells of the sample. Furthermore, in accordance with the present invention, it is critical that a specific cDNA-primer for reverse transcription (RT) of the calibrator mRNA is used as integral member of the RT-primer cocktail comprising the MAGE-specific cDNA-primers to guarantee equal assay conditions for both the different MAGE transcripts to be analysed and the reference marker.

In another preferred embodiment of the method of the present invention the normalizing reference gene serving as internal calibrator is porphobilinogen desaminase (PBGD), glyceraldehyd-3-phospat dehydrogenase (GAPDH), beta-2-microglobin or beta-actin.

In a further preferred embodiment of the method of the present invention the primer for reverse transcription of PBGD mRNA is selected from the following group of oligonucleotides:

| Primer | Sequence (5' - 3') | SEQ ID NO |
|---|---|---|
| PBGD_RT2 | CAT ACA TGC ATT CCT CAG GGT | 20 |
| PBGD_RT3 | GAA CTT TCT CTG CAG CTG GGC | 21 |
| PBGD_RT4 | TGG CAG GGT TTC TAG GGT CT | 22 |
| PBGD_RT10a | GGT TTC CCC GAA TAC TCC TG | 23 |
| PBGD_RT10d | TTG CTA GGA TGA TGG CAC TG | 24 |
| PBGD_RT12b | CCA AGA TGT CCT GGT CCT TG | 25 |
| PBGD_RT12c | CAG CAC ACC CAC CAG ATC | 26 |
| PBGD_RT12d | AGA GTC TCG GGA TCG TGC | 27 |
| PBGD_RT12e | AGT CTC GGG ATC GTG CAG | 28 |
| PBGD_RT12f | TCT CGG GAT CGT GCA GCA | 29 |
| PBGD_RT12g | ATG CAG CGA AGC AGA GTC T | 30 |
| PBGD_RT12h | CCT TTC AGC GAT GCA GCG | 31 |
| PBGD_RT13a | GTA TGC ACG GCT ACT GGC | 32 |
| PBGD_RT14a | GCT ATC TGA GCC GTC TAG AC | 33 |

-continued

| Primer | Sequence (5' - 3') | SEQ ID NO |
|---|---|---|
| PBGD_RT15a | AAT GTT ACG AGC AGT GAT GC | 34 |
| PBGD_RT15b | TGG GGC CCT GCT GGA ATG | 35 |
| PBGD_RT15e | CAG TTA ATG GGC ATC GTT AAG | 36 |
| PBGD_RT15f | ATC TGT GCC CCA CAA ACC AG | 37 |
| PBGD_RT15g | GGC CCG GGA TGT AGG CAC | 38 |
| PBGD_RT15h | GGT AAT CAC TCC CCA GAT AG | 39 |
| PBGD_RT15i | CTC CCG GGG TAA TCA CTC | 40 |
| PBGD_RT15j | CAG TCT CCC GGG GTA ATC | 41 |
| PBGD_RT15k | TGA GGA GGC AAG GCA GTC | 42 |
| PBGD_RT15l | GGA TTG GTT ACA TTC AAA GGC | 43 |

For each individual real-time MAGE RT-PCR, however, in accordance with the present invention, careful testing of candidate RT-primers specific for PBGD or the mRNA of another reference gene together with the candidate MAGE RT-primer(s) is required to end up with an optimal choice allowing the expression of the selected MAGE genes to be measured by real-time RT-PCR in comparison with reliable expression signals from the reference gene at a high level of sensitivity. Also in this case, testing of RT-primers for the highly sensitive real-time MAGE RT-PCR including the RT-primer for reverse transcription of the internal calibrator mRNA has to be carried out in the presence of the whole cocktail of RT-primers during cDNA-synthesis, in order to cope with the unpredictable interferences among different RT-primers.

In another embodiment of the method of the present invention the PCR-primers for amplification of PBGD-cDNA comprise oligonucleotides selected from the following groups:

| PBGD | Sequence (5' - 3') | SEQ ID NO |
|---|---|---|
| Sense Primer | | |
| hu_PBGD_se | AGA GTG ATT CGC GTG GGT ACC | 44 |
| PBGD_8 | GGC TGC AAC GGC GGA AGA AAA C | 45 |
| PBGD_8_F | TGC AAC GGC GGA AGA AAA C | 46 |
| PBGD_ATG-Eco | ATG TCT GGT AAC GGC AAT GC | 47 |
| Antisense Primer | | |
| PBGD_3 | TTG CAG ATG GCT CCG ATG GTG AA | 48 |
| PBGD_3.1_R | GGC TCC GAT GGT GAA GCC | 49 |
| PBGD_R | TTG GGT GAA AGA CAA CAG CAT C | 50 |

In an even more preferred embodiment of the method of the present invention oligonucleotides hu_PBGD_se and PBGD_3.1_R or hu_PBGD_se and PBGD_R are used as primer pairs for PCR-amplification of PBGD-cDNA.

Actually, to introduce PBGD as internal calibrator for quantification of MAGE transcripts by a highly sensitive real-time RT-PCR according to the present invention 24 different PBGD-specific cDNA-primers were designed and tested in the presence of the MAGE-specific cDNA-primers for efficient reverse transcription of PBGD-mRNA in a PBGD-specific real-time RT-PCR. Those PBGD-specific cDNA-primers, which gave good results in the subsequent PBGD-amplification by real-time PCR were then tested in combination with the MAGE-specific cDNA-primers in a quantitative multimarker MAGE real-time RT-PCR. However, it was found that no combination of three cDNA-primers each consisting of a pan-MAGE- and a MAGE-A1 specific cDNA-primer plus a PBGD-specific cDNA-primer led to the highly sensitive amplification of every single marker from the group consisting of MAGE-A1, -2, -3/6, -4, -10 and -12 transcripts by real-time RT-PCR (example 3). In order to solve this problem it turned out, that the reduction of cDNA-primers from a triple to a double combination was inevitable. For this purpose we had to invent an RT-protocol using very sophisticated non-standard conditions comprising unusual primer concentrations and the use of a highly selected polymerase to make a single pan-MAGE cDNA-primer work together with a PBGD cDNA-primer, without loosing the highly sensitive amplification of only a single marker in the subsequent real-time PCR (example 3). This eventually led to a final protocol for a highly sensitive quantitative multimarker MAGE real-time RT-PCR which by no means could have been anticipated from the prior art (example 5).

Accordingly, a highly preferred embodiment of the method of the present invention is related to the use of not more than two different oligonucleotides (including the RT-primer of an internal calibrator) as primers for reverse transcription in the cDNA-synthesis reaction of the real-time MAGE RT-PCR of the present invention.

In a most preferred embodiment of the method of the present invention oligonucleotides MgRT3a and/or Mg1_RT5a are used as primers for reverse transcription in the cDNA-synthesis reaction.

In a further most preferred embodiments of the method of the present invention oligonucleotides MgRT3a and PBGD_RT15b are used as primers for reverse transcription in the cDNA-synthesis reaction.

In another embodiment of the method of the present invention the MAGE- and/or the calibrator-PCR are nested or semi-nested PCRs. In order to achieve the desired high sensitivity for detection of mRNA transcribed by rare tumor cells from more than one MAGE gene, the real-time RT-PCR may be designed as nested or semi-nested PCR. For this purpose a first round of cDNA-amplification may be carried out with an appropriate pair of PCR-primers either by conventional or real-time PCR. Most preferably, this first round of PCR should not proceed to the plateau phase of amplification. Otherwise, quantification of the template content in the sample to be analyzed by the method of the present invention may become very difficult or even impossible. Moreover, it may be preferable to stop such a first round of PCR in the early or middle linear phase of amplification instead of proceeding to the late linear phase, in order to avoid interferences of an excess of preamplified PCR-products with the subsequent round of real-time PCR. Accordingly, the number of PCR-cycles and the reaction conditions that are appropriate for such a preamplification step have to be carefully optimized, respectively. In particular these parameters should be adapted to the distribution of template amounts in the collection of samples to be analyzed, to make sure, on the one hand, that the level of high sensitivity of the method of the invention is sufficient to detect MAGE in those samples showing very weak expression and, on the other hand, that quantification of MAGE in other samples showing higher expression is still feasible.

In a particularly preferred embodiment of the method of the present invention PCR-primers are used comprising pairs of oligonucleotides specifically amplifying only a single member of the selected group of MAGE genes, respectively. Despite the high homology among different members of the MAGE gene family, making the design of such monospecific oligonucleotides more difficult, a highly sensitive real-time MAGE RT-PCR for detecting the individual expression of more than one MAGE gene is highly preferable. Only thus, a quantitative expression profile of individual MAGE genes of rare disseminated tumor cells in individual cancer patients can be obtained, which may be essential for the selection of those members of the MAGE family to be included in an optimal tumor vaccine. Moreover, the prognostic impact of the expression levels of single members of the MAGE gene family may vary with different types of cancer, which can be analyzed with the real-time RT-PCR of the present invention only when pairs of PCR-primers monospecific for the cDNA of individual MAGE genes are used that do not crossamplify other members of the MAGE family.

In another embodiment of the method of the present invention PCR-primers are used comprising pairs of oligonucleotides amplifying more than one member of the selected group of MAGE genes, respectively (=pan-MAGE PCR).

Following reverse transcription real-time PCR amplification of MAGE cDNA with such consensus primers, like those suggested by Park et al. (Park, Kwon et al. 2002) may be carried out, which make use of the high level of sequence homology among the different MAGE gene transcripts. Using this or similar approaches real-time RT-PCR may lead to MAGE-amplification products derived from the transcripts of MAGE-A 1, -2, -3, -4, -6 and/or 12 expressed by as few as five cancer cells (e.g. from the human colon cancer cell line HT-29) in 10 ml of blood, while staying negative with blood from healthy donors.

For detection of the real-time PCR-amplification product(s) the sequence-independent SYBR green I method can be applied using the LightCycler System; alternatively, sequence-specific fluorescent probes, e.g. TaqMan or hybridization probes may be used. Furthermore, tissue samples (e.g. bronchoscopic biopsies) from cancer patients with different types of tumors (e.g. non-small cell lung (NSCL) cancer) may be analyzed accordingly. For this embodiment of the method of the invention it is of particular advantage that the particular way of cDNA-synthesis disclosed by the present invention makes sure that each single member of the MAGE family selected as a marker for the highly sensitive real-time RT-PCR is reliably converted from mRNA to cDNA by reverse transcription with reproducible efficiency, because due to coamplification of cDNA from different MAGE genes drop-outs of single markers at the stage of reverse transcription may easily remain unrecognized in the PCR e.g. by a positive signal derived from only one marker thus pretending successful detection of other presumably coamplified markers that indeed may have failed sufficient cDNA-synthesis although being expressed.

In another particularly preferred embodiment of the method of the present invention the PCR-primers for amplification of MAGE-cDNA comprise oligonucleotides selected from one of the following groups:

| PCR-Primer | Sequence (5' - 3') | SEQ ID NO |
|---|---|---|
| (C) | | |
| MAGE-A1 | GTA GAG TTC GGC CGA AGG AAC | 51 |
| MAGE-A1 | CAG GAG CTG GGC AAT GAA GAC | 52 |
| MAGE-A2 | CAT TGA AGG AGA AGA TCT GCC T | 53 |
| MAGE-A2 | GAG TAG AAG AAG AAG CGG T | 54 |
| MAGE-A3/6 | GAA GCC GGC CCA GGC TCG | 55 |
| MAGE-A3/6 | GAT GAC TCT GGT CAG GGC AA | 56 |
| MAGE-A4 | CAC CAA GGA GAA GAT CTG CCT | 57 |
| MAGE-A4 | TCC TCA GTA GTA GGA GCC TGT | 58 |
| MAGE-A10 | CTA CAG ACA CAG TGG GTC GC | 59 |
| MAGE-A10 | GCT TGG TAT TAG AGG ATA GCA G | 60 |
| MAGE-A12 | TCC GTG AGG AGG CAA GGT TC | 61 |
| MAGE-A12 | ATC GGA TTG ACT CCA GAG AGT A | 62 |
| (D) | | |
| MAGE-A1 | TAG AGT TCG GCC GAA GGA AC | 63 |
| MAGE-A1 | CTG GGC AAT GAA GAC CCA CA | 64 |
| MAGE-A2 | CAT TGA AGG AGA AGA TCT GCC T | 65 |
| MAGE-A2 | CAG GCT TGC AGT GCT GAC TC | 66 |
| MAGE-A3/6 | GGC TCG GTG AGG AGG CAA G | 67 |
| MAGE-A3/6 | GAT GAC TCT GGT CAG GGC AA | 68 |
| MAGE-A4 | CAC CAA GGA GAA GAT CTG CCT | 69 |
| MAGE-A4 | CAG GCT TGC AGT GCT GAC TCT | 70 |
| MAGE-A10 | ATC TGA CAA GAG TCC AGG TTC | 71 |
| MAGE-A10 | CGC TGA CGC TTT GGA GCT C | 72 |
| MAGE-A12 | TCC GTG AGG AGG CAA GGT TC | 73 |
| MAGE-A12 | GAG CCT GCG CAC CCA CCA A | 74 |

This embodiment of the invention is advantageous because it is capable of measuring the individual expression of all those members of the MAGE-A subfamily encoding target antigens recognized by cytotoxic T lymphocytes, which are thus relevant for tumor vaccination. In the particular case of MAGE-A3 and 6, which are amplified by the same pairs of PCR-primers depicted in group C and D, there is no loss of information relevant for vaccine design caused by the coamplification, because the proteins encoded by MAGE-A3 and 6 are almost identical due to a sequence homology of 99%.

In an even more preferred embodiment of the method of the present invention primers of group C are used for a first round and/or primers of group D for a second round of PCR-amplification.

This embodiment of the invention is advantagous for carrying out a highly sensitive nested or semi-nested real-time MAGE RT-PCR.

In another embodiment of the method of the present invention a single or double pair of PCR-primers is used amplifying all members of the selected group of MAGE genes, respectively. This embodiment relates to a highly sensitive real-time RT-PCR specifically detecting the expression of more than one MAGE gene, by a single pair of pan-MAGE PCR-primers in case of a single-step PCR or a double pair of pan-MAGE PCR-primers in case of a nested or semi-nested PCR. Due to the high level of sequence homology among the different MAGE genes, sites of sequence identity between all members of a selected group of MAGE genes may be found by computer-based sequence analysis, where such pan-MAGE PCR-primers can hybridize.

As with every pair of PCR-primers, either monospecific for the cDNA of an individual MAGE gene or oligospecific for the cDNAs of some or all members of a certain group of MAGE genes (=pan-MAGE PCR-primer), primer positions have to be selected in a way to avoid amplification of genomic MAGE DNA. For example, amplification of genomic MAGE-sequences can be avoided by the use of primers localized in different exons or primers spanning different neighboring exons, thus restricting hybridization to cDNA only. Furthermore, the positions of the PCR-primers have to be chosen to fall within the sequence segment(s) of the MAGE transcript(s), which is (are) reverse transcribed by the actual RT-primer(s) used for cDNA-synthesis.

The present invention further relates to a diagnostic composition comprising one or more suitable cDNA-primers for simultaneous reverse transcription of more than one different MAGE gene transcripts and optionally an appropriate calibrator mRNA in a single cDNA-synthesis reaction. The diagnostic composition of the invention is particularly useful for carrying out a variety of highly sensitive real-time MAGE RT-PCRs, thus allowing the quantification of the tumor cell load in cancer patients suffering from systemic tumor cell spread, by measuring the content of more than one kind of MAGE mRNA in blood-, bone marrow-, lymph node or other tissue samples. Moreover, the diagnostic kit is particularly useful for determining quantitative MAGE gene expression profiles of rare disseminated tumor cells in individual cancer patients, thus allowing the rational design of a MAGE-based tumor vaccine. In accordance with the present invention it is particularly preferable that at least one cDNA-primer of the diagnostic composition is MgRT3a, Mg1_RT5a or PBGD_RT15b.

Finally the present invention also relates to an oligonucleotide selected from the following group of primers:

MgRT3a
Mg1_RT5a
PBGD_RT15b

In accordance with the present invention, it was found that these oligonucleotides are particularly useful for simultaneously priming the reverse transcription of mRNA from more than MAGE genes in a single cDNA-synthesis reaction. It has been further found, in accordance with the present invention, (1) that this "single-pot" cDNA-synthesis is essential to make sure that each single member of the MAGE family selected as a marker for the highly sensitive real-time RT-PCR of the invention is reliably converted from mRNA to cDNA by reverse transcription with reproducible efficiency and (2) that only under this prerequisite the relative content in biological samples to be analyzed of the different MAGE mRNA species compared to each other can be determined or quantification of the different MAGE transcripts carried out in comparison to an internal calibrator template like the PBGD mRNA.

Definitions

| The term | |
|---|---|
| "RT" or "cDNA synthesis" | is used in the current invention for the conversion of mRNA into complementary DNA (cDNA) by a reverse transcriptase enzyme in a reverse transcription reaction (RT). |
| "RT-PCR" | is used in the current invention for methods applying a polymerase chain reaction (PCR) after converison of mRNA into complementary DNA (cDNA) by a reverse transcription reaction (RT). |
| "conventional PCR" | is used in the current invention for non-fluorescent PCR methods operated on all kinds of traditional thermocyclers. |
| "nested PCR" | is used in the current invention for PCR methods comprising two amplification steps with different sets of primers for the first and second round of amplification. |
| "semi-nested PCR" | is used in the current invention for PCR methods comprising two amplification steps with one shared primer for the first and second round of amplification. |
| "real-time PCR" | is used in the current invention for fluorescence-based PCR methods on photometric thermocyclers with the option for quantification of original template amounts. The method can include additional preamplification steps on a traditional thermocycler for a defined number of PCR-cycles. |
| "multimarker MAGE PCR" | is used in the current invention for PCR assays that enable the separate amplification of cDNA of different individual MAGE genes. |
| "pan MAGE PCR" | is used in the current invention for PCR assays that enable the amplification of cDNA of different MAGE genes by one or more pairs of consenus PCR-primers each capable of coamplifying at least two different MAGE gene transcripts. |
| "RT-primer" or "cDNA synthesis primer" | is used in the current invention for oligonucleotides designed to hybridize only to a defined target mRNA to yield specific cDNA molecules of these transcripts in a reverse transcription reaction. |
| "PCR primer" | is used in the current invention for oligonucleotides designed to hybridize only to certain regions of target cDNA to yield amplicons of a specific length in a PCR reaction. |
| "high sensitivity" | is used in the current invention for the capability of a PCR method to yield detectable MAGE specific amplificates from 5 or less tumor cells in 2 ml of whole blood. Additionally a crossing point below 30 PCR-cycles is required for real-time PCR-methods to fulfil the definition. |

REFERENCES

Chomczynski, P. and N. Sacchi (1987). "Single-step method of RNA isolation by acid guanidinium thiocyanate-phenol-chloroform extraction." *Anal Biochem* 162(1): 156-9.

Chomez, P., O. De Backer, et al. (2001). "An overview of the MAGE gene family with the identification of all human members of the family." *Cancer Res* 61(14): 5544-51.

De Plaen, E., K. Arden, et al. (1994). "Structure, chromosomal localization, and expression of 12 genes of the MAGE family." *Immunogenetics* 40(5): 360-9.

Kufer, P., Zippelius, A., Lutterbuese, R., Mecklenburg, I., Enzmann, T., Montag, A., Weckermann, D., Passlick, B., Prang, N., Reichardt, P., Dugas, M., Kollermann, M. W., Pantel, K., Riethmuller, G. (2002). "Heterogeneous Expression of MAGE-A Genes in Occult Disseminated Tumor Cells: a novel multimarker RT-PCR for diagnosis of micrometastatic disease." *Cancer Res* 62: 251-261.

Old, L. J. (2001). "Cancer/Testis (CT) antigens—a new link between gametogenesis and cancer." *Cancer Immunity* 1((30 Mar. 2001)): 1.

Park, J. W., T. K. Kwon, et al. (2002). "A new strategy for the diagnosis of MAGE-expressing cancers." *J Immunol Methods* 266(1-2): 79-86.

Scanlan, M. J., C. M. Gordon, et al. (2002). "Identification of cancer/testis genes by database mining and mRNA expression analysis." *Int J Cancer* 98(4): 485-92.

Serrano, A., B. Lethe, et al. (1999). "Quantitative evaluation of the expression of MAGE genes in tumors by limiting dilution of cDNA libraries." *Int J Cancer* 83(5): 664-9.

van der Bruggen, P., C. Traversari, et al. (1991). "A gene encoding an antigen recognized by cytolytic T lymphocytes on a human melanoma." *Science* 254(5038): 1643-7.

Yoshioka, S., Y. Fujiwara, et al. (2002). "Real-time rapid reverse transcriptase-polymerase chain reaction for intraoperative diagnosis of lymph node micrometastasis: clinical application for cervical lymph node dissection in esophageal cancers." *Surgery* 132(1): 34-40.

For Information on Standard Conditions Known in the Prior Art the Following References May be Used Sambrook, J., Russel, D., W. (2001). "Molecular Cloning—A Laboratory Manual." $3^{rd}$ edition 2001, Cold Spring Harbor Laboratory Press, Roche Molecular Biochemicals (2000). "LightCycler Operator's Manual." Version 3.5

Meuer, S., Wittwer, C., Nakagawara, K., I. (Eds.) (2001). "Rapid Cycle Real-Time PCR—Methods and Applications." Springer Publishing Dietmaier, W., Wiftwer, C., Sivasubramanian, N. (Eds.) (2002). "Rapid Cycle Real-Time PCR—Methods and Applications—Genetics and Oncology." Springer Publishing http://www.roche-applied-science.com/lightcycler-online
http://www.appliedbiosystems.com/techsupport

FIGURE LEGENDS

FIG. 1: Real-time amplification plot (A) and melting curve analysis (B) of MAGE-A1 transcripts in 2 ml of blood spiked with different numbers of Mz2-Mel cells as indicated using a standard LightCycler-DNA Master SYBR Green I protocol after oligo-dT primed cDNA synthesis. The arrows in B indicate the maximum of product dissemination over the indicated temperature range. The specific MAGE-A1 PCR product displays a melting peak at approximately 88.8° C. Unspecific products, e.g. primer dimers in this case, can be identified by their different dissociation curve. The gel electrophoresis (C) confirms specific amplification of the transcript and reliable detection of 1 tumor cell in 2 ml of whole blood.

FIG. 2: Melting curve analysis after completion of a standard LightCycler-DNA Master SYBR Green I protocol for MAGE-A2 (A) and MAGE-A12 (B) after cDNA synthesis with oligo-dT priming. At least 10 tumor cells in 2 ml of blood are required for the generation of specific PCR products, samples with lower cell numbers do not result in specific signals with this protocol.

Figure 3:
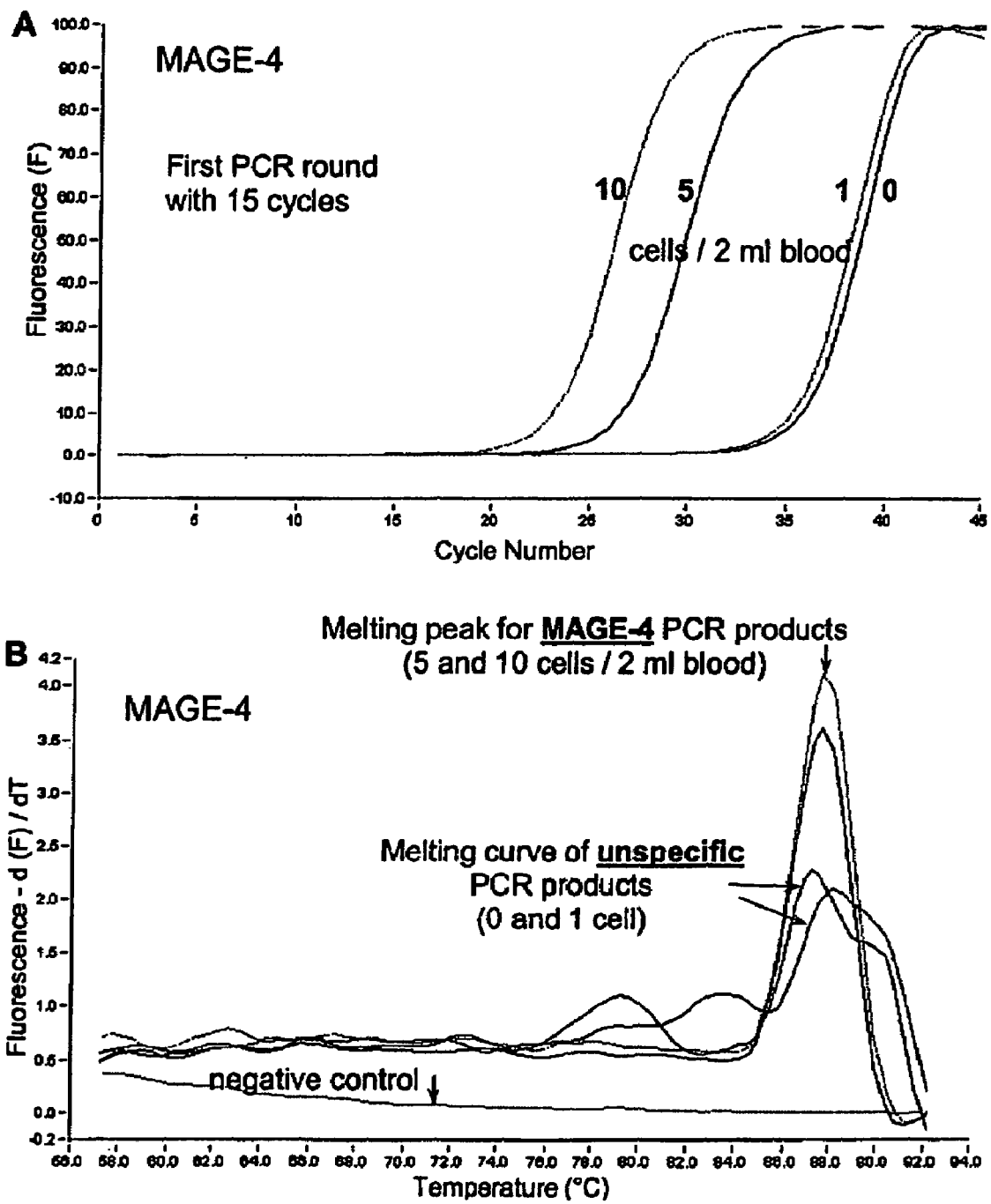

FIG. 3: Real-time amplification plot (A) and melting curve analysis (B) of MAGE-A4 mRNA in 2 ml of blood spiked with different numbers of LB-SAR cells as indicated. The first round of the nested PCR was performed with 15 cycles. Samples spiked with 5 and 10 LB-SAR cells yield the specific MAGE-A4 PCR product displaying a melting peak of approximately 87.6° C. Unspecific products obtained when spiking 1 cell or no cells can be distinguished by their different melting curves.

Figure 4:
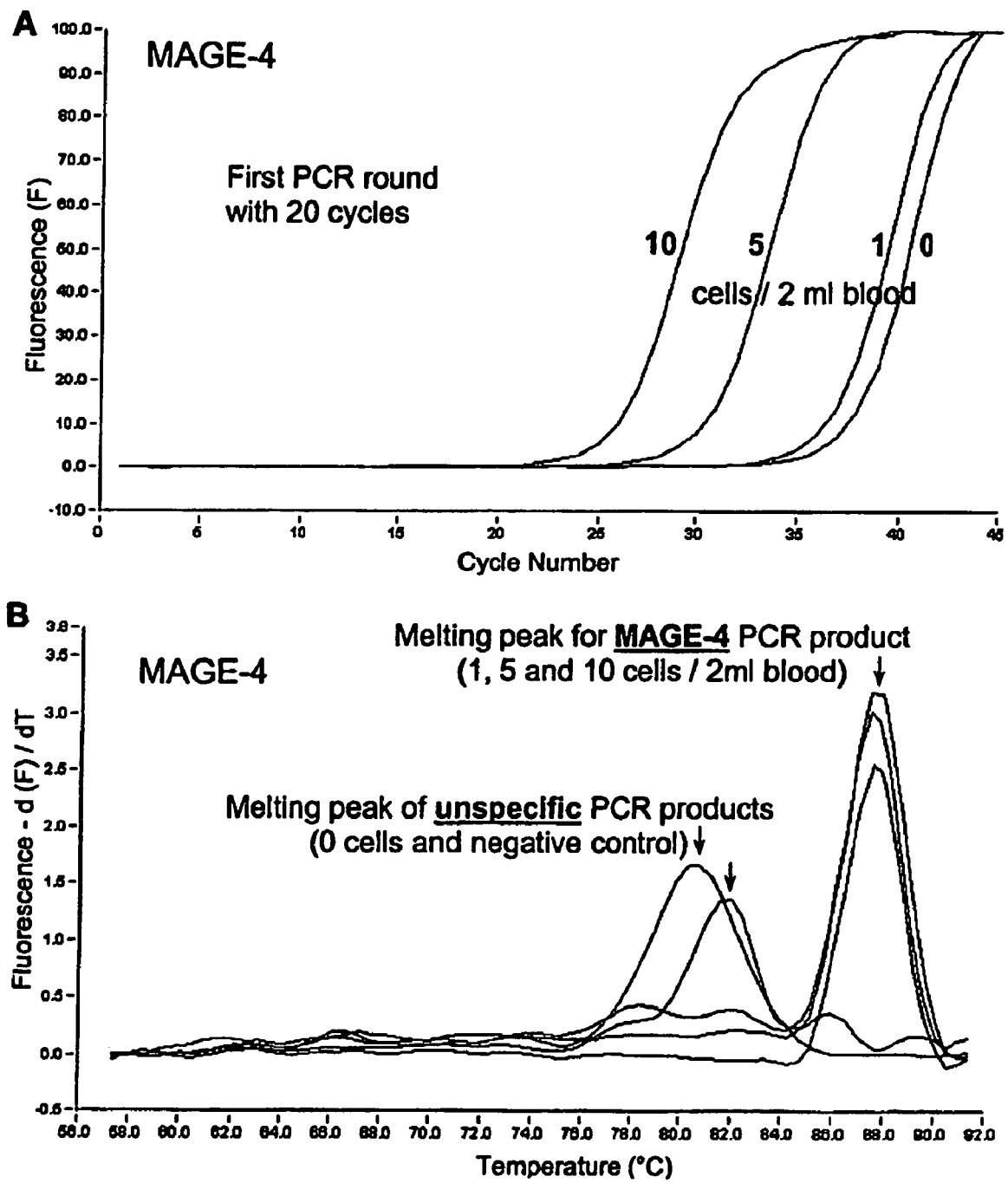

FIG. 4: Real-time amplification plot (A) and melting curve analysis (B) of the same RNA sample applied in FIG. 3 after 20 cycles of first PCR. The extension of preamplification leads to an improved sensitivity level with specific detection of MAGE-A4 PCR products when 1 LB-SAR tumor cell was diluted in 2 ml of blood. This positive achievement was associated with the increased formation of primer dimers in negative controls.

Figure 5:
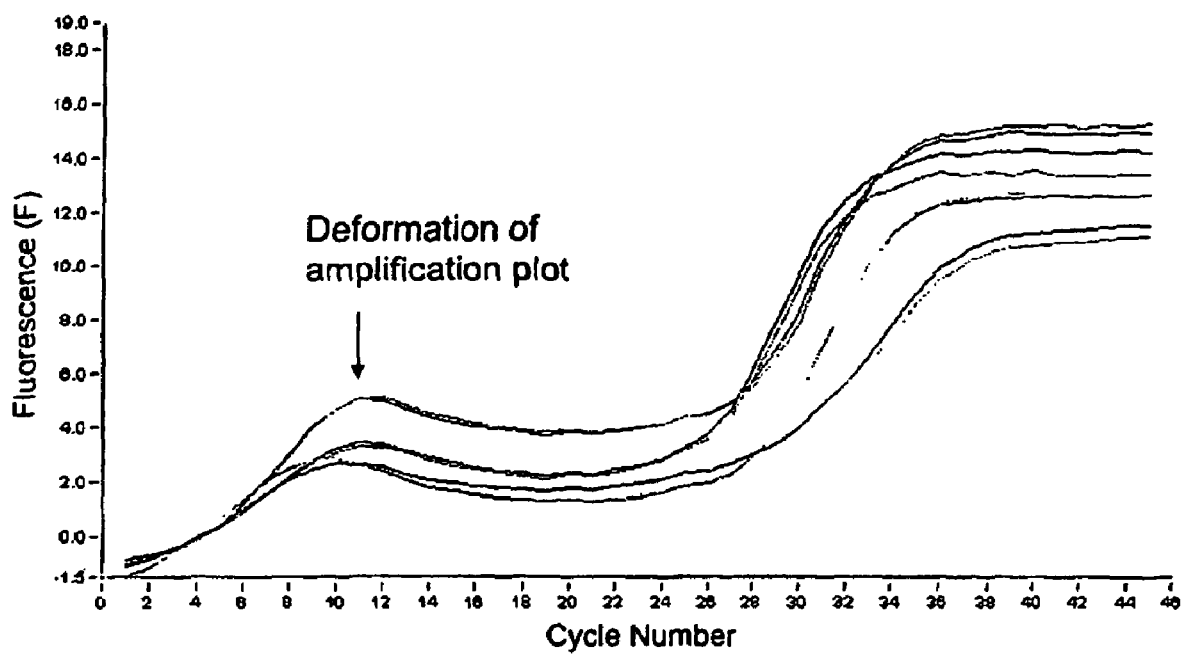

FIG. 5: Real-time amplification plot of MAGE transcripts after cDNA synthesis with a combination of antisense PCR primers for MAGE-1, -2, -3/6, -4 and -12. The application of 5 specific oligonucleotides in the reverse transcription reaction led to the formation of several unspecific products in the consecutive real-time PCR, e.g. primer dimers, associated with a deformation of the amplification curve.

Figure 6:
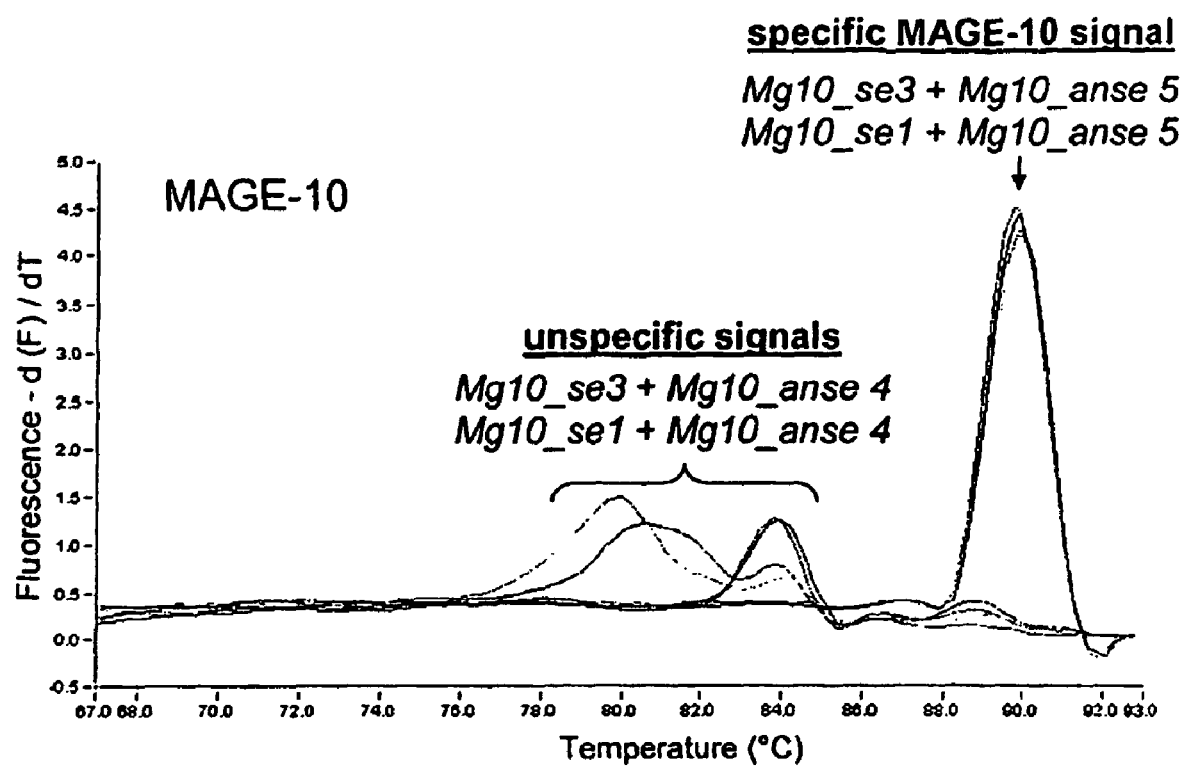

FIG. 6: Melting curve analysis of MAGE-A10 PCR products obtained with different primer-combinations for preamplification. Specific MAGE-A10 products are detectable only when a selection of two sense primers is used with a single antisense primer (Mg10_anse5). Approaches with the antisense primer Mg10_anse4 for preamplification do not result in specific signals, although this oligonucleotide could be successfully applied as antisense primer in real-time PCR.

The examples illustrate the invention.

EXAMPLE 1

Limitation of Oligo-dT Primed cDNA Synthesis for Detecting MAGE Transcripts Expressed by Rare Tumor Cells in Blood with a Real-Time Multimarker MAGE-PCR The first evaluation of a real-time MAGE PCR was performed in tumor cell dilution experiments. For this purpose we spiked 2 ml whole blood of healthy donors with different numbers of Mz2-Mel cells for amplification of MAGE-1, -2, -3/6 and -12 transcripts. To avoid degradation of the RNA each sample was immediately mixed with 10 ml denaturating nucleic acid extraction buffer [4 M guanidine isothiocyanate, 0.5% sarcosyl (N-laurylsarcosine sodium salt), 25 mM sodium citrate (pH=7.0), 0.7% 2-mercaptoethanol]. Total RNA was isolated according to the method of Chomczynski and Sacchi (Chomczynski and Sacchi 1987) and was measured-spectrophotometrically. cDNA was synthesized from 1 µg of total RNA by extension with 1.6 µg oligo-dT primer and 20 U avian myeloblastosis virus reverse transcriptase (Roche Molecular Biochemicals, Mannheim, Germany) at 25° C. for 10 min., 42° C. for 60 min. and 99° C. for 5 min.

A first PCR round for preamplification was performed in 50 µl reactions containing 5 µl of cDNA, 5 µl of 10×PCR buffer (200 mM Tris, pH=8.0, 500 mM KCl), 1.5 µl of $MgCl_2$ (50 µM), 4 µl of each dNTP (100 µM) (Invitrogen, Groningen, Netherlands), 0.2 µM of each of the outer MAGE primers, and 1.25 units of Platinum Taq DNA-Polymerase (Invitrogen) and was run on a GeneAmp PCR System 9700 (Applied Biosystems, Foster City, USA) according to the following cycle profile: enzyme activation at 95° C. for 3 min; denaturation at 95° C. for 30 s, annealing at 60° C. for 45 s and extension at 72° C. for 15 cycles followed by terminal extension at 72° C. for 7 min.

The quantification of MAGE gene expression was conducted using a LightCycler instrument and the LightCycler FastStart DNA Master SYBR Green I Kit (Roche Molecular Biochemicals, Mannheim, Germany). The inherent fluorescence of the SYBR Green I dye is enhanced 200-fold when it binds to the minor groove of double-stranded DNA. The increase in fluorescence is measured at the end of each cycle and indicates the amount of PCR products generated so far (F1, fluorescence channel 1 for SYBR Green I). Because of the labeling of any double-stranded DNA nonspecific PCR products. e.g. primer dimers, will contribute to the signal. Therefore, the resulting PCR products in the SYBR Green I protocol are verified by means of a melting-curve analysis: since the dye only binds to double-stranded DNA, the fluorescent signal decreases as the melting point of the DNA duplex is reached. Following amplification the reaction mixture is subjected to an online melting curve analysis by increasing the temperature gradually (0.1° C./s).

The real-time PCR was carried out in 15 µl reaction mixture consisting of PCR grade water with 0.9 µl MgCl$_2$ (25 mM), 1 µl of each inner MAGE primer (10 pmol/µl), 1.5 µl of FastStart DNA Master SYBR Green I and 4 µl product of the first PCR reaction. Initial denaturation at 95° C. for 5 min was followed by 45 cycles of denaturation at 95° C. for 15 s, annealing at 60° C. for 10 s and extension at 72° C. for 20 s with a temperature slope of 20° C./s performed in LightCycler capillaries. All reactions were performed in duplicates and each run included a negative control without a template.

The results of the amplification of the MAGE-A1 gene product are shown in FIG. 1: the amplification profile is depicted in FIG. 1A with fluorescence on the Y axis and the number of the PCR cycles on the X axis. The cycle number at which the amplification curve crosses the baseline of the background signals is defined as crossing point and is used for quantification of the amount of template DNA in the sample. As expected more PCR cycles are required to amplify target cDNA in a sample containing less template cDNA. In this example it takes 22 cycles before fluorescence can be detected in the blood sample spiked with 100 tumor cells, the crossing points for the samples contaminated with 10, 5 and 1 cells follow consecutively. After 39 cycles there is also increase in fluorescence for the normal blood specimen, presumably caused by unspecific amplificates or primer-dimers.

FIG. 1B shows the negative derivatives of the melting curve characteristics at the end of the PCR reaction. The peaks represent the melting points of the PCR product, i.e. the temperature at which 50% of the DNA PCR product melted. The melting curves for the MAGE-A1 PCR product display a characteristic melting point at 88.8° C. The unspecific amplificates in healthy blood, in this example primer dimers, show a different curve with a maximum at 87.5° C., enabling the discrimination of different PCR products and verification of specificity. The gel electrophoresis in FIG. 1C reconfirmes the specific amplification of the MAGE-A1 product for 1 to 100 tumor cell in 2 ml of blood.

The amplification of MAGE-A2 and -A12 did only yield specific signals when 10 tumor cells were added to 2 ml of blood. The increase of fluorescence with lower cell numbers was due to unspecific products (see FIGS. 2A and 2B).

Because of the lack of MAGE-A4 expression in Mz2-Mel cells we also spiked 2 ml whole blood of healthy donors with different numbers of LB-SAR cells that express MAGE-4 in a stable manner. The protocol was the same as described above but we used 2 µl of cDNA for PCR. The results of the amplification of the MAGE-4 gene product are shown in FIG. 3. Any samples with less than 5 tumor cells per 2 ml did not result in specific detection of MAGE expression (FIG. 3A). For 5 and 10 cells per 2 ml the real-time PCR yields the spefific MAGE-4 PCR product with a melting point of approximately 87.6° C., the melting curves for 0 and 1 cell reveal the amplification of unspecific products (FIG. 3B).

To improve the sensitivity of the test we added 5 cycles to the protocol of the first PCR. The detection threshold was decreased thereby to 1 tumor cell/2 ml of blood yielding specific MAGE-A4 products for all tumor cell dilutions (FIG. 4A). However, the increase in PCR cycles was accompanied by primer-dimer formation causing a melting peak for the negative control without a template (FIG. 4B). A further addition of PCR cylces for preamplification was impossible because of the reaching of a plateau phase with impracticability of consecutive quantification of gene expression.

This example shows the feasibility to detect the expression of single MAGE genes by real-time PCR, but it moreover clearly demonstrates the difficulty to ensure the amplification of all relevant MAGE mRNA species. Oligo-dT primed cDNA synthesis appears to prefer single mRNA molecules while omitting others. This property leads to the complete drop out of several parameters with a dramatic decrease in sensitivity to detect rare transcripts. The addition of more cycles in the first PCR round cannot completely compensate this loss because of the increasing appearance of unspecific products. PCR methods using consensus MAGE primers after reverse transcription with oligo-dT are especially susceptible for this considerable problem, because the putative "pan-MAGE" approach would only amplify some of the available MAGE transcripts. Altough the standard protocol for reverse transcription using oligo-dT primer is able to generate successful amplification of MAGE-A1 transcripts it is not applicable for cDNA synthesis when screening for expression of the whole gene family.

EXAMPLE 2

Superiority of Highly Selected MAGE-Specific Primers for cDNA-Synthesis Prior to Amplification of MAGE by a Real-Time Multimarker PCR With the intention to establish a method for the sensitive detection of all MAGE mRNA subtypes and simultaneously decrease unspecific background we modified the AMV reverse transcription protocol by using a combination of the outer antisense PCR primers for MAGE-1, -2, -3/6, -4 and -12 in 2.5 µM solution for specific cDNA synthesis. After preamplification with 20 cycles in a first PCR round the real-time PCR revealed a deformation of the amplification plot (FIG. 5). The purification of the first PCR product led to the reconstitution of the regular amplification curve, presuming an overdosing of different oligonucleotides in the cDNA synthesis that causes interference of fluorescence in real-time PCR, although this approach could be shown to work in conventional PCR (Kufer 2002). The combination of several antisense primers for RT recation seems not to be an applicable approach for our purposes.

This accentuates the need for a specific shared oligonucleotide for reverse transcription of all MAGE-A mRNAs. We screened the MAGE-A sequences for universal segments by computer based sequence analysis and evaluated nine different oligonucleotides for their ability to act as sensitive pan-MAGE primer for the detection of MAGE-A transcripts in a 2 ml blood sample contaminated with 5 tumor cells (Mz2-Mel cells for MAGE-1, -2, -3/6 and -12; LB-SAR cells for MAGE-4) (Table 2). We used the standard 1$^{st}$ strand cDNA Synthesis Kit for RT-PCR (AMV) supplied by Roche Molecular Biochemicals (Mannheim, Germany) in 20 µl with 2 µl of 10× Reaction buffer, 5 mM MgCl$_2$, 1 mM of dNTP mixture, 50 units of RNAse inhibitor, 20 units of AMV reverse transcriptase and 1 µg of RNA according to the manufacturer's protocol and added specific oligonucleotide primers in 2.5 µM concentration. The synthesis was performed in a GeneAmp PCR System 9700 (Applied Biosystems, Foster City, USA) for 10 min at 25° C., 60 min at 42° C. and 5 min at 99° C. Only one oligonucleotide turned out to be suitable for a reliable binding to all relevant MAGE-A mRNAs (Table 3), the other candidates as well as Oligo-dT, random hexamers or the combination of antisense PCR primers caused the drop out of at least one marker or displayed low sensitivity ($C_T$-values>30). However, the transcription of the entire MAGE-A mRNAs by this single primer was accompanied by a late crossing-point for MAGE-A1 leading to poor sensitivity for this relevant marker.

In an attempt to improve the sensitivity for detection of the important MAGE-A1 marker we evaluated several additional reverse transcription primers specific for the synthesis of MAGE-A1 cDNA to be combined with the prior established pan-MAGE primer within the same protocol (Table 4). Again only one out of eleven combinations was able to amplify all relevant MAGE mRNA species, the other compositions showed drop outs of at least one marker (Table 5). Primer combinations failing to transcribe MAGE-A1 mRNA were excluded from further examination ("not determined" in the table). Meanwhile we included the MAGE-A10 marker to the protocol as decribed in example 4, nevertheless the combination of RT primers MgRT3a and Mg1_RT5a allowed the specific reverse transcription of all relevant MAGE-A mRNAs and the subsequent amplification in real-time PCR with much higher sensitivity than oligo-dT or random hexamers. This approach accomplishes the cDNA synthesis of the complete MAGE transcriptome and is therefore the prerequisite for sensitive PCR assays, irrespective of the used primers or PCR strategy.

Here we could document the detection of all relevant MAGE markers expressed in 5 tumor cells spiked into 2 ml of whole blood. Furthermore the MAGE expression can be quantified using external standard curves or a direct comparison of single markers.

EXAMPLE 3

Quantification of MAGE Expression by Use of an Internal Calibrator

The reliable quantification of gene expression implies the inclusion of an internal calibrator, e.g. a non-regulated housekeeping gene, to exclude variations in sample size or quality. Therefore we meant to quantify MAGE expression in relative comparison to the expression of a housekeeping gene, e.g. porphobilinogen-desaminase (PBGD). For this purpose we evaluated a broad variety of PBGD RT primers (Table 6) to integrate the reverse transcription of PBGD mRNA into the established cDNA synthesis protocol described in example 2. Primers that failed to yield specific amplification of PBGD transcripts were excluded from further evaluation. We tested 21 different PBGD specific oligonucleotides in combination with the prior established RT primers MgRT3a+Mg1_RT5a, but only one combination using the primer PBGD_RT10b resulted in the successful generation of specific PCR products of all examined MAGE markers and PBGD (Table 7). However, the combination of three oligonucleotides in cDNA synthesis was linked to a markedly decreased sensitivity (crossing-points >30 cycles for MAGE-2 and -12), thus appearing not to be an applicable approach when using real-time PCR subsequently. Therefore we were forced to evaluate further protocols with fewer than three RT primers.

Searching for more sensitive reverse transcriptase enzymes we tested the single pan-MAGE primer MgRT3a in two additional Kits for cDNA synthesis in a new experiment with 1 µg of total RNA from 2 ml of blood spiked with 5 tumor cells (Mz2-Mel cells for MAGE-1, -2, -3/6, -10, -12 and LB-SAR cells for MAGE-4). The ThermoScript RT-PCR Kit supplied by Invitrogen (Groningen, Netherlands) completely failed to create any amplifiable MAGE cDNA when we followed the standard protocol of the manufacture (Table 8), even though the Kit was designed for reverse transcription of difficult templates.

Additionally we applied an Omniscript RT Kit (Qiagen, Hilden, Germany) using the single pan-MAGE primer MgRT3a in 2.5 µM solution [with 2 µl of 10× Buffer RT, dNTPs 0.5 mM each, 10 units of RNAse Inhibitor (Roche) and 4 units of Omniscript RT (Qiagen) for 60 min at 37° C. and 5 min. at 93° C.] and could generate amplifyable cDNA of all relevant MAGE mRNAs and PBGD mRNA. The direct comparison of the Omniscript RT Kit to the prior used AMV Kit demonstrated a significantly higher sensitivity for the Omniscript RT reaction without drop outs of single parameters when analyzing identical aliquots of the same RNA preparation (Table 8).

This new protocol was tested on it's compatibility with various PBGD RT primers (Table 6) after the isolation of total RNA from 2 ml of blood spiked with 10 tumor cells. Combinations that failed to generate a positive PBGD signal were excluded from further evaluation (quoted as "not determined" in the table). Only one out of 32 oligonucleotides (PBGD_RT15b) did not disturb the reverse transcription of MAGE mRNAs while efficiently mediates the conversion of PBGD mRNA into cDNA (Table 9). The second best candidate (PBGD_RT13a) already failed to generate the same results when the sensitivity threshold was increased to 5 tumor cells/2 ml blood. The crossing-point ($C_T$) differences clearly represent the varying levels of MAGE expression in the tumor cells with low amounts of MAGE-A10 and -A12 transcripts and high quantity of MAGE-A1 and -A4 mRNA in the utilized cell cultures as published in the literature (Serrano, Lethe et al. 1999). The expression level of each particular MAGE gene can be quoted as $C_T^{MAGE}/C_T^{PBGD}$ and can therefore balance variations between individual samples. For the first time this protocol allows the reflection of the actual proportions of MAGE gene expression in striking contrast to the prior art.

EXAMPLE 4

Detection of MAGE-A10 Transcripts Expressed by Rare Tumor Cells in Blood Using Real-Time MAGE RT-PCR In the first evaluation of the MAGE genes it was assumed that MAGE-A10 expression is only present at very low levels and therefore neglectable as marker for cancerous conditions. After the detection of MAGE-A10 specific cytolytic lymphocytes (Huang LQ, Brasseur F et al. 1999) the re-evaluation of expression profiles in tumor cells demonstrated weak but frequent transcription of the MAGE-A10 gene (Serrano, Lethe et al. 1999). Therefore it was our objective to include MAGE-A10 as another additional sensitive marker in the described Multimarker MAGE RT PCR.

A selection of different sense and antisense primers specific for MAGE-A10 cDNA were designed (Table 10) and tested for their potential to generate a MAGE-A10 PCR product. We isolated total RNA from 2 ml of whole blood contaminated with 100 Mz2-Mel cells and performed cDNA synthesis with the MAGE-RT primers MgRT3a and Mg1RT5a as described in example 2. The PCR was carried out in 50 µl reactions with 10× PCR buffer (Invitrogen), dNTP mixture 0.2 µM each (Invitrogen), 1.5 µM MgCl$_2$, 1.25 units Platinum Taq DNA Polymerase (Invitrogen) and 2 µl of cDNA for 40 cycles (initial enzyme activation at 95° C. for 3 min, denaturation at 95° C. for 30 sec, annealing at 60° C. for 45 sec, elongation at 72° C. for 60 sec and final extension at 72° C. for 7 min). The PCR products were analyzed by electrophoresis in a 30% polyacrylamide gel and stained with ethidium bromide. Several primer combinations yielded specific MAGE-A10 PCR products (Table 11A). The most promising combinations were further evaluated for application in real-time PCR using a LightCycler FastStart SYBR Green I Kit. The reaction was performed in capillaries with a total volume of 15 µl, 0.66 µM PCR primer each and 2.5 mM MgCl$_2$ concentration for 50 cycles (initial enzyme activation at 95° C. for 5 min, denaturation at 95° C. for 15 sec, annealing at 60° C. for 10 sec and elongation at 72° C. for 20 sec). The results demonstrated 6 successful primer combinations for the amplification of MAGE-A10 mRNA in the LightCycler system (Table 11B) that were used to construct a sensitive nested PCR for the detection of 5 Mz2-Mel cells in 2 ml of blood. Four different combinations were tested in a first PCR round with 20 cycles and subsequent real-time PCR analysis with the nested primer set Mg10_se3+Mg10_anse2. All experiments containing Mg10_anse4 as antisense primer in the first PCR round failed to yield specific amplification (FIG. 6), therefore primer sets including Mg10_se5 as antisense primer in the first PCR are the only possible composition. The sense primers Mg10_se1 or Mg10_se3 can be successfully used for the first and second round of a nested or semi-nested PCR.

EXAMPLE 5

Analysis of Blood and Bone Marrow Samples of Cancer Patients with a Highly Sensitive Multimarker MAGE Real-Time RT-PCR After careful optimization of the reaction conditions we tested blood and bone marrow samples from patients with localized prostate cancer for disseminated tumor cells with the multimarker MAGE real-time RT-PCR. 1 ml of bone marrow aspirate and 2 ml of blood were stabilized and prepared according to example 1. Total RNA was resuspended in 50 µl of DEPC-treated water and 10 µl were utilized in the subsequent cDNA synthesis using the Omniscript RT Kit (Qiagen, Hilden, Germany) in 20 µl with 2 µl of 10× Buffer RT, 2 µl of the supplied dNTP mix, 1 µl of MgRT3a (50 pmol/µl) and PBGD_RT15b primer (50 pmol/µl), 10 units of RNAse inhibitor (Roche) and 4 units of Omniscript RT enzyme. The reaction was executed in a GeneAmp PCR System 9700 (Applied Biosystems, Foster City, USA) for 60 min at 37° C. followed by denaturation at 93° C. for 5 min.

2 µl of the cDNA were used for the first round of PCR in 20 µl reactions with 2 µl of 10× PCR Buffer, 0.6 µl MgCl$_2$ (50 µM), 1.6 µl dNTP mix and 0.2 µl Platinum Taq DNA polymerase (all by Invitrogen, Groningen, Netherlands) and 0.4 µl of each outer MAGE primer (10 pmol/µl) according to the protocol described in example 1. For the real-time PCR we prepared 15 µl reactions in LightCycler capillaries with 1.5 µl of FastStart DNA Master SYBR Green I reagent, 2 µl of the first PCR product and different concentrations of MgCl$_2$ and each inner MAGE primer: for MAGE-A1 we used 2.5 mM MgCl$_2$ and 1 µM inner MAGE-A1 primers, for MAGE-A2 and -A10 3 mM MgCl$_2$ and 1.2 µM inner MAGE-A2 or -A10 primers, for MAGE-A3/6 and -4 2.5 mM MgCl$_2$ and 1.2 µM inner MAGE-A3/6 or -4 primers, and for MAGE-A12 3 mM MgCl$_2$ and 0.8 µM inner MAGE-A12 primers. The reaction was run for 5 min at 95° C. for initial activation of the enzyme, 10 sec at 95° C. for denaturation, 5 sec at 60° C. for annealing and 10 sec at 72° C. for elongation for 40 cycles. After completion of the reaction the PCR products were subjected to a melting curve analysis spanning 65° C. to 95° C. with a ramping rate of 0.1° C./s and confirmed with electrophoresis on 30% acrylamide gels in ambiguous cases.

The amplification of PBGD mRNA was performed in a separate real-time PCR in 20 µl with 1 µl of cDNA, 5 mM MgCl$_2$, 0.5 µM of sense primer (5'-AGA GTG ATT CGC GTG GGT ACC-3' (SEQ ID NO:44), 0.5 µM of antisense primer (5'-TTG GGT GAA AGA CAA CAG CAT C-3' (SEQ ID NO:50) and 2 µl of FastStart DNA Master SYBR Green I (Roche). The protocol was modified as follows: initial enzyme activation for 5 min at 95° C. denaturation for 15 sec at 95° C., annealing at 60° C. for 10 sec and extension for 20 sec at 72° C. After completion of the PCR the products were subjected to a melting curve analysis as described before. In total we were able to screen two groups of patients with prostate cancer after radical prostatectomy:

(a) 21 patients with attested biochemical relapse after radical prostatectomy defined as rising serum PSA level >0.5 ng/ml in the absence of any signs for local tumor growth. These patients bear a high risk for developing metastatic disease because of systemic spread of disseminated PSA producing tumor cells.

(b) 18 patients without biochemical relapse after radical prostatectomy defined as serum PSA level <0.5 ng/ml and presentation of a low risk profile for systemic tumor spread (i.e. Gleason score 6 and preoperative serum PSA level 20 ng/ml and tumor stage pT$_1$ or pT$_2$, pN$_0$, R$_0$) and postoperative survival >30 months at the time of sample collection. In these patients the development of metastatic disease should be an unlikely event.

In the high risk group we could identify 14 patients (=66%, Table 12) with the expression of at least one MAGE gene in at least one sample (bilateral bone marrow aspirates or blood). The low risk group displayed MAGE expression in samples of 7 patients (=38%, Table 13). Furthermore the total number of positive tests as well as the expression level was much higher in the high risk than in the low risk cohort. It must be emphasized that the low risk group does not represent a true "negative" or "control" group, since these patients also had malignant disease. Because of the generally long disease free survival time of patients with prostate cancer the detection of MAGE gene expression in the low risk group can be interpreted as true positive results with evidence for systemic tumor spread before clinical manifestation of metastatic disease at the present time. The quantity of MAGE expression can add further prognostic value, but the potency of these parameter has to be assessed after completion of the follow-up period of the cohort. The analysis of this cohort provides an impressive prove of principle for the sensitive detection and quantification of several individual MAGE markers by the real-time RT-PCR of the present invention and the exemplified use of this method for early diagnosis of minimal residual tumor disease.

TABLE 1

Members of the MAGE gene family showing restricted expression in malignant tumors and testicular germ cells only.

| Gene Subfamily | Gene Name |
|---|---|
| MAGE-A | hMAGE-A1 |
|  | hMAGE-A2 |
|  | hMAGE-A3 |
|  | hMAGE-A4 |
|  | hMAGE-A5 |
|  | hMAGE-A6 |
|  | hMAGE-A8 |
|  | hMAGE-A9 |
|  | hMAGE-A10 |
|  | hMAGE-A11 |
|  | hMAGE-A12 |

TABLE 1-continued

Members of the MAGE gene family showing restricted expression in malignant tumors and testicular germ cells only.

| Gene Subfamily | Gene Name |
|---|---|
| MAGE-B | hMAGE-B1 |
|  | hMAGE-B2 |
|  | hMAGE-B3 |
|  | hMAGE-B4 |
|  | hMAGE-B5 |
|  | hMAGE-B6 |
|  | hMAGE-B10 |
|  | hMAGE-B16 |
|  | hMAGE-B17 |
| MAGE-C | hMAGE-C1 |
|  | hMAGE-C2 |
|  | hMAGE-C3 |
|  | hMAGE-C4 |

| Primer | Sequence (5' - 3') | SEQ ID NO |
|---|---|---|
| MgRT1a | CCA GCA TTT CTG CCT TTG TGA | 1 |
| MgRT1b | CCA GCA TTT CTG CCT GTT TG | 2 |
| MgRT2 | CAG CTC CTC CCA GAT TT | 3 |
| MgRT3a | ACC TGC CGG TAC TCC AGG | 4 |
| MgRT3b | ACC TGC CGG TAC TCC AGG TA | 5 |
| MgRT4 | GCC CTT GGA CCC CAC AGG AA | 6 |
| MgRT5a | AGG ACT TCA CAT AGC TGG TTC A | 7 |
| MgRT5b | GGA CTT TCA CAT AGC TGG TTT C | 8 |
| MgRT6 | TTT ATT CAG ATT TAA TTT C | 9 |

TABLE 3

Evaluation of different primers for cDNA synthesis: Crossing-Points for the detection of MAGE mRNA by a multimarker MAGE real-time RT-PCR.

| RT-Primer | MAGE-1 | MAGE-2 | MAGE-3/6 | MAGE-4 | MAGE-12 |
|---|---|---|---|---|---|
| random hexamer | 33.3 | n.d. | n.d. | n.d. | n.d. |
| Oligo-dT | 30.1 | — | 27.0 | 30.2 | — |
| 3' primer combination | 30.2 | 24.8 | 26.5 | 23.7 | — |
| MgRT1a | 28.8 | — | — | 31.4 | — |
| MgRT1b | — | 22.0 | 20.9 | 35.1 | — |
| MgRT2 | — | 24.17 | 23.0 | 29.9 | 34.5 |
| MgRT3a | 30.2 | 22.7 | 19.8 | 21.7 | 22.1 |
| MgRT3b | 28.7 | — | — | 21.8 | — |
| MgRT4 | — | 23.4 | 22.4 | 20.7 | — |
| MgRT5a | 27.6 | — | 20.6 | 22.4 | — |
| MgRT5b | 28.4 | — | — | 20.0 | — |
| MgRT6 | — | — | 21.6 | — | 25.0 |

"n.d." = not determined, "—" = negative signal

| Primer | Sequence (5' - 3') | SEQ ID NO |
|---|---|---|
| Mg1_RT1 | CAA GAG ACA TGA TGA CTC TC | 10 |
| Mg1_RT2 | TTC CTC AGG CTT GCA GTG CA | 11 |
| Mg1_RT3 | GAG AGG AGG AGG AGG TGG C | 12 |
| Mg1_RT4 | GAT CTG TTG ACC CAG CAG TG | 13 |
| Mg1_RT5a | CAC TGG GTT GCC TCT GTC | 14 |
| Mg1_RT5c | CTG GGT TGC CTC TGT CGA G | 15 |
| Mg1_RT5d | GGG TTG CCT CTG TCG AGT G | 16 |
| Mg1_RT5e | GGC TGC TGG AAC CCT CAC | 17 |
| Mg1_RT6 | GCT TGG CCC CTC CTC TTC AC | 18 |
| Mg1_RT7 | GAA CAA GGA CTC CAG GAT AC | 19 |

TABLE 5

Combination of pan-MAGE RT primer MgRT3a with different MAGE-A1 specific RT primers for cDNA synthesis: Crossing-Points for the detection of MAGE mRNA by a multimarker MAGE real-time RT-PCR.

| RT-Primer: MgRT3a+ | MAGE-1 | MAGE-2 | MAGE-3/6 | MAGE-4 | MAGE-10 | MAGE-12 |
|---|---|---|---|---|---|---|
| Mg1 outer 3' | 20.6 | 23.9 | 23.2 | n.d. | — | — |
| Mg1 RT1 | 19.8 | — | 21.7 | n.d. | n.d. | — |
| Mg1 RT2 | — | 21.5 | 19.5 | n.d. | n.d. | — |
| Mg1 RT3 | — | n.d. | n.d. | n.d. | n.d. | n.d. |
| Mg1 RT4 | — | n.d. | n.d. | n.d. | n.d. | n.d. |
| Mg1 RT5a | 20.7 | 22.1 | 12.1 | 20.9 | 23.5 | 23.5 |
| Mg1 RT5c | 20.3 | 28.7 | 29.3 | n.d. | — | — |
| Mg1 RT5d | 22.1 | 21.3 | 29.3 | n.d. | — | — |
| Mg1 RT5e | 22.2 | 25.0 | 33.7 | n.d. | 24.1 | 22.8 |
| Mg1 RT6 | — | n.d. | n.d. | n.d. | n.d. | n.d. |
| Mg1 RT7 | 22.0 | 26.2 | 20.9 | n.d. | 25.9 | — |

"n.d." = not determined, "—" = negative signal

| Primer | Sequence (5' - 3') | SEQ ID NO |
|---|---|---|
| PBGD_R | TTG GGT GAA AGA CAA CAG CAT C | 50 |
| PBGD_3 | TTG CAG ATG GCT CCG ATG GTG AAG | 75 |
| PBGD_3.1R | GGC TCC GAT GGT GAA GCC | 49 |
| PBGD_RT1 | AAC TCC TGC TGC TCG TCC AG | 76 |
| PBGD_RT2 | CAT ACA TGC ATT CCT CAG GGT | 20 |
| PBGD_RT3 | GAA CTT TCT CTG CAG CTG GGC | 21 |
| PBGD_RT4 | TGG CAG GGT TTC TAG GGT CT | 22 |
| PBGD_RT5 | TTG TGC CAG CCC ATG CGC TG | 77 |
| PBGD_10a | GGT TTC CCC GAA TAC TCC TG | 23 |
| PBGD_10b | AGC TTC CGA AGC CGG GTG | 78 |
| PBGD_10d | TTG CTA GGA TGA TGG CAC TG | 24 |
| PBGD_12a | CTT GGC TCG CAC TTC CAC G | 79 |
| PBGD_12b | CCA AGA TGT CCT GGT CCT TG | 25 |
| PBGD_12c | CAG CAC ACC CAC CAG ATC | 26 |
| PBGD_12d | AGA GTC TCG GGA TCG TGC | 27 |
| PBGD_12e | AGT CTC GGG ATC GTG CAG | 28 |
| PBGD_12f | TCT CGG GAT CGT GCA GCA | 29 |
| PBGD_12g | ATG CAG CGA AGC AGA GTC T | 30 |
| PBGD_12h | CCT TTC AGC GAT GCA GCG | 31 |
| PBGD_13a | GTA TGC ACG GCT ACT GGC | 32 |
| PBGD_14a | GCT ATC TGA GCC GTC TAG AC | 33 |
| PBGD_14b | GCA GGG ACA TGG ATG GTA G | 80 |
| PBGD_15a | AAT GTT ACG AGC AGT GAT GC | 34 |
| PBGD_15b | TGG GGC CCT CGT GGA ATG | 35 |
| PBGD_15c | AGC CAA CTG GGG CCC TCG | 81 |
| PBGD_15d | TAA GCT GCC GTG CAA CAT CC | 82 |
| PBGD_15e | CAG TTA ATG GGC ATC GTT AAG | 36 |
| PBGD_15f | ATC TGT GCC CCA CAA ACC AG | 37 |
| PBGD_15g | GGC CCG GGA TGT AGG CAC | 38 |
| PBGD_15h | GGT AAT CAC TCC CCA GAT AG | 39 |
| PBGD_15i | CTC CCG GGG TAA TCA CTC | 40 |
| PBGD_15j | CAG TCT CCC GGG GTA ATC | 41 |
| PBGD_15k | TGA GGA GGC AAG GCA GTC | 42 |
| PBGD_15l | GGA TTG GTT ACA TTC AAA GGC | 43 |

TABLE 7

Combination of primers MgRT3a and Mg1_RT5a with PBGD specific RT primers for cDNA synthesis: Crossing-Points for the detection of PBGD and MAGE mRNA by a multimarker MAGE real-time RT-PCR.

| RT-Primer: MgRT3a + Mg1_RT5a+ | PBGD | MAGE-1 | MAGE-2 | MAGE-3/6 | MAGE-4 | MAGE-10 | MAGE-12 |
|---|---|---|---|---|---|---|---|
| PBGD_R | — | — | 24.5 | 24.9 | 20.9 | n.d. | 21.9 |
| PBGD_3 | — | 20.3 | 21.8 | 20.1 | n.d. | n.d. | — |
| PBGD_3.1_R | — | — | 22.6 | 20.2 | n.d. | n.d. | — |
| PBGD_RT1 | — | n.d. | n.d. | n.d. | n.d. | n.d. | n.d. |
| PBGD_RT2 | 14.3 | 22.3 | 21.8 | — | n.d. | n.d. | 28.7 |
| PBGD_RT3 | 13.4 | 23.0 | 22.6 | 20.3 | n.d. | n.d. | — |
| PBGD_RT4 | — | n.d. | n.d. | n.d. | n.d. | n.d. | n.d. |
| PBGD_RT5 | — | n.d. | n.d. | n.d. | n.d. | n.d. | n.d. |
| PBGD_RT10a | — | n.d. | n.d. | n.d. | n.d. | n.d. | n.d. |
| PBGD_RT10b | 13.0 | 23.2 | 31.6 | 21.3 | n.d. | 24.6 | 33.3 |
| PBGD_RT10d | 14.1 | 22.7 | 23.8 | 21.1 | n.d. | — | 30.0 |
| PBGD_RT12a | — | n.d. | n.d. | n.d. | n.d. | n.d. | n.d. |
| PBGD_RT12b | 14.4 | 29.0 | 21.6 | 32.0 | n.d. | — | — |
| PBGD_RT12c | 14.6 | 28.0 | 20.8 | >36 | n.d. | — | >36 |
| PBGD_RT12d | 15.2 | 26.0 | 22.3 | >36 | n.d. | — | >36 |
| PBGD_RT12e | 14.3 | 26.8 | 23.2 | 21.2 | n.d. | — | >36 |
| PBGD_RT12f | 14.6 | 21.2 | — | 21.9 | n.d. | — | — |
| PBGD_RT12g | 14.9 | 21.8 | 29.4 | 23.3 | n.d. | — | 22.6 |
| PBGD_RT12h | 15.2 | — | 22.7 | 21.5 | n.d. | — | — |
| PBGD_RT13a | 14.0 | — | 23.5 | — | n.d. | — | 24.5 |
| PBGD_RT15a | 14.5 | 21.9 | 25.8 | 20.9 | n.d. | — | 31.3 |

"n.d." = not determined,
"—" = negative signal

TABLE 8

Evaluation of different reverse transcriptase enzymes: Crossing-Points for the detection of PBGD and MAGE mRNA by a multimarker MAGE real-time RT-PCR.

| RT Enzyme: | MAGE-1 | MAGE-2 | MAGE-3/6 | MAGE-4 | MAGE-10 | MAGE-12 |
|---|---|---|---|---|---|---|
| Thermoscript (Invitrogen) | — | — | — | n.d. | — | — |
| AMV (Roche) | — | 26.0 | 19.4 | n.d. | — | 22.3 |
| Omniscript (Qiagen) | 19.6 | 22.1 | 19.8 | 16.9 | 23.8 | 21.5 |

"n.d." = not determined,
"—" = negative signal

TABLE 9

Combination of pan-MAGE RT 42primer MgRT3a with different PBGD RT primers using the Omniscript RT protocol: Crossing-Points for the detection of PBGD and MAGE mRNA by a multimarker MAGE real-time RT-PCR.

| RT Primer: MgRT3a+ | PBGD | 43 MAGE-1 | MAGE-2 | MAGE-3/6 | MAGE-4 | MAGE-10 | MAGE-12 |
|---|---|---|---|---|---|---|---|
| PBGD_R | — | n.d. | n.d. | n.d. | n.d. | n.d. | n.d. |
| PBGD_RT1 | — | n.d. | n.d. | n.d. | n.d. | n.d. | n.d. |
| PBGD_RT2 | 22.7 | — | n.d. | n.d. | n.d. | n.d. | — |
| PBGD_RT3 | 18.9 | — | n.d. | n.d. | n.d. | n.d. | — |
| PBGD_RT4 | 19.8 | — | n.d. | n.d. | n.d. | n.d. | — |
| PBGD_RT5 | — | n.d. | n.d. | n.d. | n.d. | n.d. | n.d. |
| PBGD_RT10a | 16.3 | — | n.d. | n.d. | n.d. | n.d. | — |
| PBGD_RT10b | — | n.d. | n.d. | n.d. | n.d. | n.d. | n.d. |
| PBGD_RT10d | 22.6 | — | n.d. | n.d. | n.d. | n.d. | — |
| PBGD_RT12a | — | n.d. | n.d. | n.d. | n.d. | n.d. | n.d. |
| PBGD_RT12b | 18.0 | — | n.d. | n.d. | n.d. | n.d. | — |
| PBGD_RT12c | 21.6 | 21.0 | — | 32.2 | n.d. | 35.7 | — |
| PBGD_RT12d | 25.6 | 21.6 | 25.1 | 30.1 | n.d. | — | — |
| PBGD_RT12e | 18.6 | 22.2 | 23.0 | 25.8 | n.d. | — | — |
| PBGD_RT12f | 20.8 | 22.8 | — | 30.1 | n.d. | — | — |
| PBGD_RT12g | 22.9 | — | n.d. | n.d. | n.d. | n.d. | — |
| PBGD_RT12h | 23.6 | 20.3 | 22.1 | 26.7 | n.d. | — | — |
| PBGD_RT13a | 21.4 | 21.1 | 23.7 | 20.1 | n.d. | 30.0 | 25.6 |
| PBGD_RT14a | 23.7 | 22.8 | 29.2 | 27.0 | n.d. | — | >33 |
| PBGD_RT14b | — | — | n.d. | n.d. | n.d. | n.d. | — |
| PBGD_RT15a | 23.8 | 19.7 | 25.9 | 22.0 | n.d. | — | 24.6 |
| PBGD_RT15b | 20.2 | 20.3 | 22.2 | 28.9 | 23.1 | 25.5 | 21.7 |
| PBGD_RT15c | — | n.d. | n.d. | n.d. | n.d. | n.d. | n.d. |
| PBGD_RT15d | — | — | n.d. | n.d. | n.d. | n.d. | — |
| PBGD_RT15e | 18.5 | 20.3 | 22.0 | 33.0 | n.d. | — | 23.9 |
| PBGD_RT15f | 19.9 | 19.8 | 27.0 | 18.0 | n.d. | 22.6 | — |
| PBGD_RT15g | 18.5 | 21.2 | 23.3 | 29.0 | n.d. | — | — |
| PBGD_RT15h | 22.7 | — | n.d. | n.d. | n.d. | n.d. | — |
| PBGD_RT15i | 22.0 | — | 26.2 | 19.8 | n.d. | — | — |
| PBGD_RT15j | 24.6 | 18.8 | 20.7 | 25.7 | n.d. | — | — |
| PBGD_RT15k | 22.7 | 18.7 | 20.0 | 26.5 | n.d. | — | 22.3 |
| PBGD_RT15l | 24.2 | — | 21.8 | 26.6 | n.d. | 23.2 | 19.6 |

"n.d." = not determined,
"—" = negative signal

| Primer | Sequence (5' - 3') | SEQ ID NO |
|---|---|---|
| Mg10_se1 | CTA CAG ACA CAG TGG GTC GC | 83 |
| Mg10_se2 | GCA GGA TCT GAC AAG AGT CC | 84 |
| Mg10_se3 | ATC TGA CAA GAG TCC AGG TCC | 85 |
| Mg10_anse1 | TGG GAG TGT GGG CAG GAC T | 86 |
| Mg10_anse2 | CGC TGA CGC TTT GGA GCT C | 87 |
| Mg10_anse3 | ATC CTC CTC CAC AGC CAG G | 88 |
| Mg10_anse4 | GGA GCT GGT GGA AGT GGA TG | 89 |
| Mg10_anse5 | GCT TGG TAT TAG AGG ATA GCA G | 90 |
| Mg10_anse6 | CAT CAG CAG AAA CCT CCT CTG | 91 |
| Mg10_anse7 | AAT GGA AGG GAA GCA ACG ACC | 92 |
| Mg10_anse8 | GGA GCC CTC ATC AGA TTG ATC | 93 |

TABLE 11

Combination of MAGE-A1046specific sense and antisense PCR primer

| primer combination | Mg10_se1+ | Mg10_se2+ | Mg10_se3+ |
|---|---|---|---|
| Results of conventional RT-PCR with 40 cycles using total RNA isolated from 2 ml of blood spiked with 100 Mz2/Mel cells. | | | |
| Mg10_anse1 | – | – | + |
| Mg10_anse2 | + | – | +++ |
| Mg10_anse3 | – | – | + |
| Mg10_anse4 | ++ | + | ++ |
| Mg10_anse5 | ++ | + | ++ |
| Mg10_anse6 | + | + | + |
| Mg10_anse7 | + | (+) | + |
| Mg10_anse8 | – | – | + |

TABLE 11-continued

Combination of MAGE-A1046specific sense and antisense PCR primer

| primer combination | Mg10_se1+ | Mg10_se2+ | Mg10_se3+ |
|---|---|---|---|
| Results of real-time PCR with 50 cycles using total RNA isolated from 2 ml of blood spiked with 100 Mz2/Mel cells: Crossing-Points for the detection of MAGE-A10 mRNA by a multimarker MAGE real-time RT-PCR | | | |
| Mg10_anse2 | | n.d. | 37.4 |
| Mg10_anse4 | | 33.7 | 35.8 |
| Mg10_anse5 | | 38.9 | 39.9 |
| Mg10_anse6 | | n.d. | 40.8 |

"(+)" - "+++" = intensity of specific signal, "–" = no signal

TABLE 12

Crossing-Points for the47detection of PBGD and MAGE mRNA by multimarker MAGE real-time RT-PCR in blood and bone marrow aspirates of patients with confirmed relapse of prostate cancer.

| patient | CK-ICC | samples | PBGD | MAGE-1 | MAGE-2 | MAGE-3/6 | MAGE-4 | MAGE-10 | MAGE-12 |
|---|---|---|---|---|---|---|---|---|---|
| 1. | neg | BM right | 26.1 | — | — | — | — | — | — |
| | | BM left | 26.6 | — | — | — | — | — | — |
| | | Blood | 22.4 | — | — | — | — | — | — |
| 2. | pos | BM right | 26.2 | — | — | — | — | — | — |
| | | BM left | 24.8 | — | — | — | — | — | — |
| | | Blood | 21.7 | — | 24.5 | — | — | — | — |
| 3. | neg | BM right | 23.8 | — | — | — | — | — | — |
| | | BM left | 23.8 | — | — | — | — | — | — |
| | | Blood | — | — | — | — | — | — | — |
| 4. | neg | BM right | 21.8 | — | 24.5 | — | — | — | — |
| | | BM left | 23.6 | — | — | — | — | — | — |
| | | Blood | 22.6 | — | — | — | — | — | — |
| 5. | neg | BM right | 20.8 | — | 23.9 | — | — | — | — |
| | | BM left | 24.2 | — | — | — | — | — | — |
| | | Blood | 23.3 | — | — | >36 | — | — | — |
| 6. | neg | BM right | 23.5 | — | — | — | — | — | — |
| | | BM left | 21.9 | — | — | — | — | — | — |
| | | Blood | 21.7 | — | — | — | — | — | — |
| 7. | neg | BM right | 26.2 | — | — | — | — | — | — |
| | | BM left | 24.2 | — | — | — | — | — | — |
| | | Blood | 20.0 | — | — | — | — | — | — |
| 8. | neg | BM right | 28.2 | 23.7 | 11.8 | — | 33.0 | — | — |
| | | BM left | 26.9 | — | — | — | — | — | — |
| | | Blood | 22.7 | — | — | — | 29.4 | — | — |
| 9. | pos | BM right | 24.1 | — | — | — | — | — | — |
| | | BM left | 25.0 | — | — | — | — | — | — |
| | | Blood | 23.1 | — | — | — | — | — | — |
| 10. | pos | BM right | 20.9 | — | — | — | — | — | — |
| | | BM left | 20.2 | — | — | — | — | — | — |
| | | Blood | 24.9 | — | — | — | — | — | — |
| 11. | neg | BM right | 22.8 | — | — | — | 29.2 | — | — |
| | | BM left | 21.2 | — | — | — | — | — | — |
| | | Blood | 22.4 | — | — | — | — | — | — |
| 12. | neg | BM right | 27.3 | — | — | — | — | — | — |
| | | BM left | 24.7 | — | — | — | — | — | — |
| | | Blood | 21.6 | — | — | — | — | — | — |
| 13. | neg | BM right | — | — | — | — | — | — | — |
| | | BM left | 27.0 | 19.1 | — | — | — | — | — |
| | | Blood | 23.1 | — | — | — | — | — | — |
| 14. | neg | BM right | 24.3 | 13.2 | — | — | — | — | — |
| | | BM left | 24.1 | 12.6 | 23.8 | — | — | — | — |
| | | Blood | 24.1 | — | — | — | — | — | — |
| 15. | neg | BM right | 24.1 | <7.0 | 23.6 | — | >36 | — | — |
| | | BM left | 24.0 | 7.2 | — | — | — | — | — |
| | | Blood | 22.6 | — | — | — | — | — | — |
| 16. | neg | BM right | — | — | — | — | — | — | — |
| | | BM left | 25.5 | 18.5 | 28.8 | — | >36 | — | — |
| | | Blood | 22.1 | — | — | — | — | — | — |
| 17. | neg | BM right | 23.0 | — | — | >36 | 29.4 | — | — |
| | | BM left | 29.5 | — | — | 19.5 | — | — | — |
| | | Blood | 22.6 | — | — | — | — | — | — |

TABLE 12-continued

Crossing-Points for the47detection of PBGD and MAGE mRNA by multimarker MAGE real-time RT-PCR in blood and bone marrow aspirates of patients with confirmed relapse of prostate cancer.

| patient | CK-ICC | samples | PBGD | MAGE-1 | MAGE-2 | MAGE-3/6 | MAGE-4 | MAGE-10 | MAGE-12 |
|---|---|---|---|---|---|---|---|---|---|
| 18. | neg | BM right | 26.1 | — | — | 19.3 | — | — | 22.0 |
|  |  | BM left | 24.6 | — | — | — | — | — | — |
|  |  | Blood | 21.8 | 21.2 | 27.5 | — | — | — | — |
| 19. | neg | BM right | 24.2 | — | — | — | 16.7 | — | — |
|  |  | BM left | 25.0 | — | — | — | — | — | — |
|  |  | Blood | n.a. |  |  |  |  |  |  |
| 20. | neg | BM right | 24.1 | — | — | — | — | — | — |
|  |  | BM left | 26.7 | — | — | — | — | — | — |
|  |  | Blood | 21.5 | — | — | — | — | 32.4 | — |
| 21. | neg | BM right | 23.0 | — | — | — | 10.6 | 30.9 | 9.8 |
|  |  | BM left | 30.3 | — | — | 21.0 | <7.0 | — | 13.1 |
|  |  | Blood | 20.7 | — | — | — | — | — | — |

CK-ICC = cytokeratin-immunocytochemistry,
BM = bone marrow aspirate

TABLE 13

Crossing-Points for the49detection of PBGD and MAGE mRNA by multimarker MAGE real-time RT-PCR in blood and bone marrow aspirates of patients with low risk for relapse of prostate cancer.

| patient | CK-ICC | samples | PBGD | MAGE-1 | MAGE-2 | MAGE-3/6 | MAGE-4 | MAGE-10 | MAGE-12 |
|---|---|---|---|---|---|---|---|---|---|
| 1. | pos | BM right | 20.0 | — | — | — | — | — | — |
|  |  | BM left | 21.6 | — | — | — | — | — | — |
|  |  | Blood | 23.0 | — | — | — | — | — | — |
| 2. | neg | BM right | 20.4 | — | — | — | — | — | — |
|  |  | BM left | 19.4 | — | — | — | — | — | — |
|  |  | Blood | 20.1 | — | — | — | — | — | — |
| 3. | neg | BM right | 29.0 | — | — | — | — | — | — |
|  |  | BM left | 27.1 | — | — | — | — | — | — |
|  |  | Blood | 29.6 | — | — | — | — | — | — |
| 4. | neg | BM right | 26.5 | — | — | — | — | — | — |
|  |  | BM left | 24.7 | — | — | — | — | — | — |
|  |  | Blood | 21.2 | — | — | — | — | — | — |
| 5. | neg | BM right | 25.2 | 21.4 | — | — | — | — | — |
|  |  | BM left | 25.7 | 21.8 | — | — | — | — | — |
|  |  | Blood | 22.3 | — | — | — | — | — | — |
| 6. | neg | BM right | 26.8 | — | — | — | — | — | — |
|  |  | BM left | 27.3 | — | — | — | — | — | — |
|  |  | Blood | 23.7 | — | — | — | >36 | — | — |
| 7. | pos | BM right | 22.0 | — | — | — | — | — | — |
|  |  | BM left | 21.7 | — | — | — | — | — | — |
|  |  | Blood | 22.9 | — | — | — | — | — | — |
| 8. | neg | BM right | 23.1 | — | — | — | — | — | — |
|  |  | BM left | 22.2 | — | — | — | — | — | — |
|  |  | Blood | 22.2 | — | — | — | — | — | — |
| 9. | neg | BM right | 35.5 | — | — | — | 30.1 | — | — |
|  |  | BM left | — | — | — | — | — | — | — |
|  |  | Blood | 22.1 | — | — | — | — | — | — |
| 10. | neg | BM right | 24.1 | — | — | — | — | — | — |
|  |  | BM left | 29.6 | — | — | — | — | — | — |
|  |  | Blood | 22.8 | — | — | — | — | — | — |
| 11. | neg | BM right | 23.4 | — | — | — | — | — | — |
|  |  | BM left | 22.7 | — | — | — | — | — | — |
|  |  | Blood | 22.7 | — | — | — | — | — | — |
| 12. | neg | BM right | — | — | — | — | — | — | — |
|  |  | BM left | 24.0 | — | — | — | — | — | — |
|  |  | Blood | 23.5 | — | — | — | >36 | — | — |
| 13. | neg | BM right | >36 | — | — | — | — | — | — |
|  |  | BM left | 25.0 | 18.9 | — | — | 20.6 | — | — |
|  |  | Blood | n.a. |  |  |  |  |  |  |
| 14. | neg | BM right | 27.6 | 23.9 | — | — | — | — | — |
|  |  | BM left | 24.8 | — | — | — | — | — | — |
|  |  | Blood | 24.4 | — | — | — | — | — | — |
| 15. | neg | BM right | 30.4 | — | — | — | — | — | — |
|  |  | BM left | 26.9 | — | — | — | — | — | — |
|  |  | Blood | 21.5 | — | — | — | — | — | — |

TABLE 13-continued

Crossing-Points for the 49 detection of PBGD and MAGE mRNA by multimarker MAGE real-time RT-PCR in blood and bone marrow aspirates of patients with low risk for relapse of prostate cancer.

| patient | CK-ICC | samples | PBGD | MAGE-1 | MAGE-2 | MAGE-3/6 | MAGE-4 | MAGE-10 | MAGE-12 |
|---|---|---|---|---|---|---|---|---|---|
| 16. | neg | BM right | — | — | — | — | — | — | — |
|  |  | BM left | 23.2 | — | — | — | — | — | — |
|  |  | Blood | 21.9 | — | — | — | — | — | — |
| 17. | neg | BM right | 26.3 | 14.7 | 18.5 | — | 28.2 | — | 29.6 |
|  |  | BM left | 31.2 | 13.2 | — | — | 20.8 | — | — |
|  |  | Blood | 21.8 | — | — | — | >36 | — | — |
| 18. | neg | BM right | 24.3 | — | — | — | — | — | — |
|  |  | BM left | 24.6 | — | — | — | — | — | — |
|  |  | Blood | 21.2 | — | — | — | — | — | — |

CK-ICC = cytokeratin-immunocytochemistry,
BM = bone marrow aspirate

The invention claimed is:

1. A real-time RT-PCR method for specifically detecting the expression of more than one MAGE gene comprising reverse transcribing multiple different MAGE transcripts simultaneously in a single cDNA-synthesis reaction using a cDNA-primer MgRT3a consisting of SEQ ID NO:4.

2. A diagnostic composition comprising a cDNA-primer MgRT3a consisting of SEQ ID NO:4.

3. An oligonucleotide designated MgRT3a (SEQ ID NO:4).

4. The diagnostic composition of claim 2, further comprising one or more of the primers Mg1_RT5a (SEQ ID NO:14), MgRT2 (SEQ ID NO:3), MgRT1b (SEQ ID NO: 2), MgRT4 (SEQ ID NO: 6), MgRT6 (SEQ ID NO: 9), MgRT1a (SEQ ID NO: 1), MgRT3b (SEQ ID NO: 5), MgRT5b (SEQ ID NO: 8), Mg1_RT1 (SEQ ID NO: 10), Mg1_RT2 (SEQ ID NO: 11), Mg1_RT3 (SEQ ID NO: 12), Mg1_RT4 (SEQ ID NO: 13), Mg1_RT5c (SEQ ID NO: 15), Mg1_RT5d (SEQ ID NO: 16), Mg1_RT5e (SEQ ID NO: 17), Mg1_RT6 (SEQ ID NO: 18), and Mg1_RT7 (SEQ ID NO: 19).

5. The diagnostic composition of claim 2, the composition further comprising cDNA primers that hybridize to a calibrator mRNA for reverse transcription of a calibrator mRNA.

6. The diagnostic composition of claim 5, wherein the calibrator mRNA is porphobilinogen desaminase (PBGD) mRNA.

7. The diagnostic composition of claim 6, wherein the composition further comprises primer PBGD RT15b (SEQ ID NO: 35).

8. The diagnostic composition of claim 6, wherein said PCR-primers for amplification of PBGD-cDNA comprise the oligonucleotides hu PBGD se (SEQ ID NO:44) and PGBD R (SEQ ID NO:50).

9. The diagnostic composition of claim 2, further comprising PCR-primers for amplification of MAGE-cDNA, the primers comprising oligonucleotides selected from one of the following groups:

| PCR-primer | Sequence (5' - 3') |
|---|---|
| (A) | |
| MAGE-A1 | GTA GAG TTC GGC CGA AGG AAC (SEQ ID NO:51) |
| MAGE-A1 | CAG GAG CTG GGC AAT GAA GAC (SEQ ID NO:52) |
| MAGE-A2 | CAT TGA AGG AGA AGA TCT GCC T (SEQ ID NO:53) |
| MAGE-A2 | GAG TAG AAG AAG AAG AAG CGG T (SEQ ID NO:54) |
| MAGE-A3/6 | GAA GCC GGC CCA GGC TCG (SEQ ID NO:55) |
| MAGE-A3/6 | GAT GAC TCT GGT CAG GGC AA (SEQ ID NO:56) |
| MAGE-A4 | CAC CAA GGA GAA GAT CTG CCT (SEQ ID NO:57) |
| MAGE-A4 | TCC TCA GTA GTA GGA GCC TGT (SEQ ID NO:58) |
| MAGE-A10 | CTA CAG ACA CAG TGG GTC GC (SEQ ID NO:59) |
| MAGE-A10 | GCT TGG TAT TAG AGG ATA GCA G (SEQ ID NO:60) |
| MAGE-A12 | TCC GTG AGG AGG CAA GGT TC (SEQ ID NO:61) |
| MAGE-A12 | ATC GGA TTG ACT CCA GAG AGT A (SEQ ID NO:62) |
| (B) | |
| MAGE-A1 | TAG AGT TCG GCC GAA GGA AC (SEQ ID NO:63) |
| MAGE-A1 | CTG GGC AAT GAA GAC CCA CA (SEQ ID NO:64) |
| MAGE-A2 | CAT TGA AGG AGA AGA TCT GCC T (SEQ ID NO:65) |
| MAGE-A2 | CAG GCT TGC AGT GCT GAC TC (SEQ ID NO:66) |
| MAGE-A3/6 | GGC TCG TGA GGA GGC AA G (SEQ ID NO:67) |
| MAGE-A3/6 | GAT GAC TCT GGT CAG GGC AA (SEQ ID NO:68) |
| MAGE-A4 | CAC CAA GGA GAA GAT CTG CCT (SEQ ID NO:69) |
| MAGE-A4 | CAG GCT TGC AGT GCT GAC TCT (SEQ ID NO:70) |
| MAGE-A10 | ATC TGA CAA GAG TCC AGG TTC (SEQ ID NO:71) |
| MAGE-A10 | CGC TGA CGC TTT GGA GCT C (SEQ ID NO:72) |
| MAGE-A12 | TCC GTG AGG AGG CAA GGT TC (SEQ ID NO:73) |
| MAGE-A12 | GAG CCT GCG CAC CCA CCA A (SEQ ID NO:74) |

\* \* \* \* \*

UNITED STATES PATENT AND TRADEMARK OFFICE
CERTIFICATE OF CORRECTION

PATENT NO. : 7,491,814 B2  Page 1 of 1
APPLICATION NO. : 10/536932
DATED : February 17, 2009
INVENTOR(S) : Peter Kufer and Ingo Mecklenburg It is certified that error appears in the above-identified patent and that said Letters Patent is hereby corrected as shown below:

In column 10, line 11, SEQ ID NO:54, delete
"GAG TAG AAG AAG AAG CGG T" and insert
--GAG TAG AAG AGG AAG AAG CGG T-- therefor.

In column 49, Sequence: 54, delete
"gagtagaaga agaagcggt" and insert
--gagtagaaga ggaagaagcg gt-- therefor.

In claim 9, column 63, line 16, SEQ ID NO:54, delete
"GAG TAG AAG AAG AAG CGG T" and insert
--GAG TAG AAG AGG AAG AAG CGG T-- therefor.

Signed and Sealed this

Second Day of June, 2009

JOHN DOLL
*Acting Director of the United States Patent and Trademark Office*